(12) United States Patent
Chattopadhyay et al.

(10) Patent No.: US 7,674,957 B2
(45) Date of Patent: Mar. 9, 2010

(54) STRESS RESPONSIVE TRANSCRIPTION FACTOR INVOLVED IN PLANT GROWTH AND DEVELOPMENT AND METHODS THEREOF

(75) Inventors: Sudip Chattopadhyay, New Delhi (IN); Vandana Yadav, New Delhi (IN)

(73) Assignee: National Centre for Plant Genome Research, New Delhi (IN)

( * ) Notice: Subject to any disclaimer, the term of this patent is extended or adjusted under 35 U.S.C. 154(b) by 419 days.

(21) Appl. No.: 11/522,893

(22) Filed: Sep. 19, 2006

(65) Prior Publication Data

US 2007/0266459 A1 Nov. 15, 2007

(30) Foreign Application Priority Data

May 9, 2006 (IN) .................. 1146/DEL/2006

(51) Int. Cl.
*C12N 15/29* (2006.01)
*C12N 15/82* (2006.01)
*C12N 5/04* (2006.01)
*A01H 5/00* (2006.01)
*A01H 5/10* (2006.01)

(52) U.S. Cl. .................. 800/298; 536/23.6; 435/320.1; 435/410; 800/320.1; 800/317.4; 800/278; 800/294; 800/290

(58) Field of Classification Search ....................... None
See application file for complete search history.

(56) References Cited

U.S. PATENT DOCUMENTS 7,345,217 B2 * 3/2008 Zhang et al. ................. 800/289

OTHER PUBLICATIONS

Mallappa et al (2006, Journal of Biological Chemistry 281(31):22190-22199).*
Bowie et al, Science 247:1306-1310, 1990.*
McConnell et al, Nature 411 (6838):709-713, 2001.*
Schepens, I, Duek, P and Fankhauser, C, Phytochrome-Mediated Light Signalling in *Arabdopsis*, Current Opinion in Plant Biology, 7:564-569 (2004), Elsevier Ltd.
Martinez-Garcia, JF, Huq, E and Quail, PH, Direct Targeting of Light Signals to a Promoter Element-Bound Transcription Factor, Science, 288:859-863 (2000), American Association for the Advancement of Science.
Nagy, F and Schafer, E, Phytochromes Control Photomorphogenesis by Differentially Regulated, Interacting Signaling Pathways in Higher Plants, Annu. Rev. Plant Biol., 53:329-355 (2002), Annual Reviews.
Thiele, A, Herold, M, Lenk, I, Quail, PH and Gatz, C, Heterologous Expression of Arabidopsis Phytochrome B in Transgenic Potato Influences Photosynetic Performance and Tuber Development, Plant Physiology, 120:73-81 (1999), American Society of Plant Physiologists.

Liu, Y, Roof, S, Ye, Z, Barry, C, van Tuinen, A, Vrebalov, J, Bowler, C and Giovannoni, J, Manipulation of Light Signal Transduction as a Means of Modifying Fruit Nutritional Quality in Tomato, Proc. Natl. Acad. Sci. USA, 101(26):9897-9902 (2004), National Academy of Sciences.
Ma, L, Li, J, Qu, L, Hager, J, Chen, Z, Zhao, H and Deng, XW, Light Control of Arabidopsis Development Entails Coordinated Regulation of Genome Expression and Cellular Pathways, The Plant Cell, 13:2589-2607 (2001), American Society of Plant Biologists.
Tepperman, JM, Zhu, T, Chang, H-S, Wang, X and Quail, PH, Multiple Transcription-Factor Genes are Early Targets of Phytochrome A Signaling, Proc. Natl. Acad. Sci. USA, 98(16):9437-9442 (2001), National Academy of Sciences.
Terzaghi, WB and Cashmore, AR, Light-Regulated Transcription, Annu. Rev. Plant Physiol. Plant Mol. Biol., 46:445-474 (1995), Annual Reviews.
Puente, P. Wei, N. and Deng, XW, Combinatorial Interplay of Promoter Elements Constitutes the Minimal Determinants for Light and Developmental Control of Gene Expression in *Arabidopsis*, The EMBO Journal, 15(14):3732-3743 (1996), European Molecular Biology Organization.
Yadav, V, Kundu, S, Chattopadhyay, D, Negi, P, Wei, N, Deng, X-W and Chattopadhyay, S, Light Regulated Modulation of Z-Box Containing Promoters by Photoreceptors and Downstream Regulatory Components, COP1 and HY5, in *Arabidopsis*, The Plant Journal, 31(6):741-753 (2002), Blackwell Science Ltd.
Tobin, EM and Kehoe, DM, Phytochrome Regulated Gene Expression, Seminars in Cell Biology, 5:335-346 (1994), Academic Press Ltd.
Wang, Z-Y, Kenigsbuch, D, Sun, L, Harel, E, Ong, MS and Tobin, EM, A Myb-Related Transcription Factor Is Involved in the Phytochrome Regulation of an *Arabidopsis Lhcb* Gene, The Plant Cell, 9:491-507 (1997), American Society of Plant Physiologists.
Abe, H, Urao, T, Ito, T, Seki, M, Shinozaki, K and Yamaguchi-Shinozaki, K, Arabidopsis AtMYC2 (bHLH) and AtMYB2 (MYB) Function as Transcriptional Activators in Abscisic Acid Signaling, The Plant Cell, 15:63-78 (2003), American Society of Plant Biologists.

(Continued)

*Primary Examiner*—Stuart F. Baum
(74) *Attorney, Agent, or Firm*—Jyoti C. Iyer

(57) ABSTRACT

The disclosure relates to transgenic plants over-expressing a unique light-regulated transcription factor, Z-box binding factor involving in plant growth and development, found in plant. Overexpression of the Z-box binding factor in plant results in early flowering, lateral root development and increased tolerance to environmental and abiotic stresses compared to wild type and mutant plants. The disclosure further provides identification and functional characterization of Z-box binding factor. The disclosure also provides a method for modifying a plant's traits, such as enhanced productivity and increased tolerance to environmental and abiotic stresses.

31 Claims, 5 Drawing Sheets

OTHER PUBLICATIONS

Ledent, V and Vervoort, M, The Basic Helix-Loop-Helix Protein Family: Comparative Genomics and Phylogenetic Analysis, Genome Research, 11:754-770 (2001), Cold Spring Harbor Laboratory Press.

Yadav, V, Mallappa, C, Gangappa, SN, Bhatia, S and Chattopadhyay, S, A Basic Helix-Loop-Helix Transcription Factor in Arabidopsis, MYC2, Acts as a Repressor of Blue Light-Mediated Photomorphogenic Growth, The Plant Cell, 17:1953-1966 (2005), American Society of Plant Biologists.

Holm, M, MA, L-G, Qu, L-J and Deng, X-W, Two Interacting bZIP Proteins are Direct Targets of COP1-Mediated Control of Light-Dependent Gene Expression in *Arabidopsis*, Genes and Development, 16:1247-1259 (2002), Cold Spring Harbor Laboratory Press.

Lorenzo, O, Chico, JM, Sanchez-Serrano, JJ and Solano, R, *Jasmonate-Insensitivei* Encodes a MYC Transcription Factor Essential to Discriminate between Different Jasmonate-Regulated Defense Responses in Arabidopsis, The Plant Cell, 16:1938-1950 (2004), American Society of Plant Biologists.

Ha,S-B and Gynheung, A, Identification of Upstream Regulatory Elements Involved in the Developmental Expression of the *Arabidopsis thaliana cab1* Gene, Proc. Natl. Acad. Sci. USA, 85:8017-8021 (1988), National Academy of Sciences.

* cited by examiner

Figure: 2

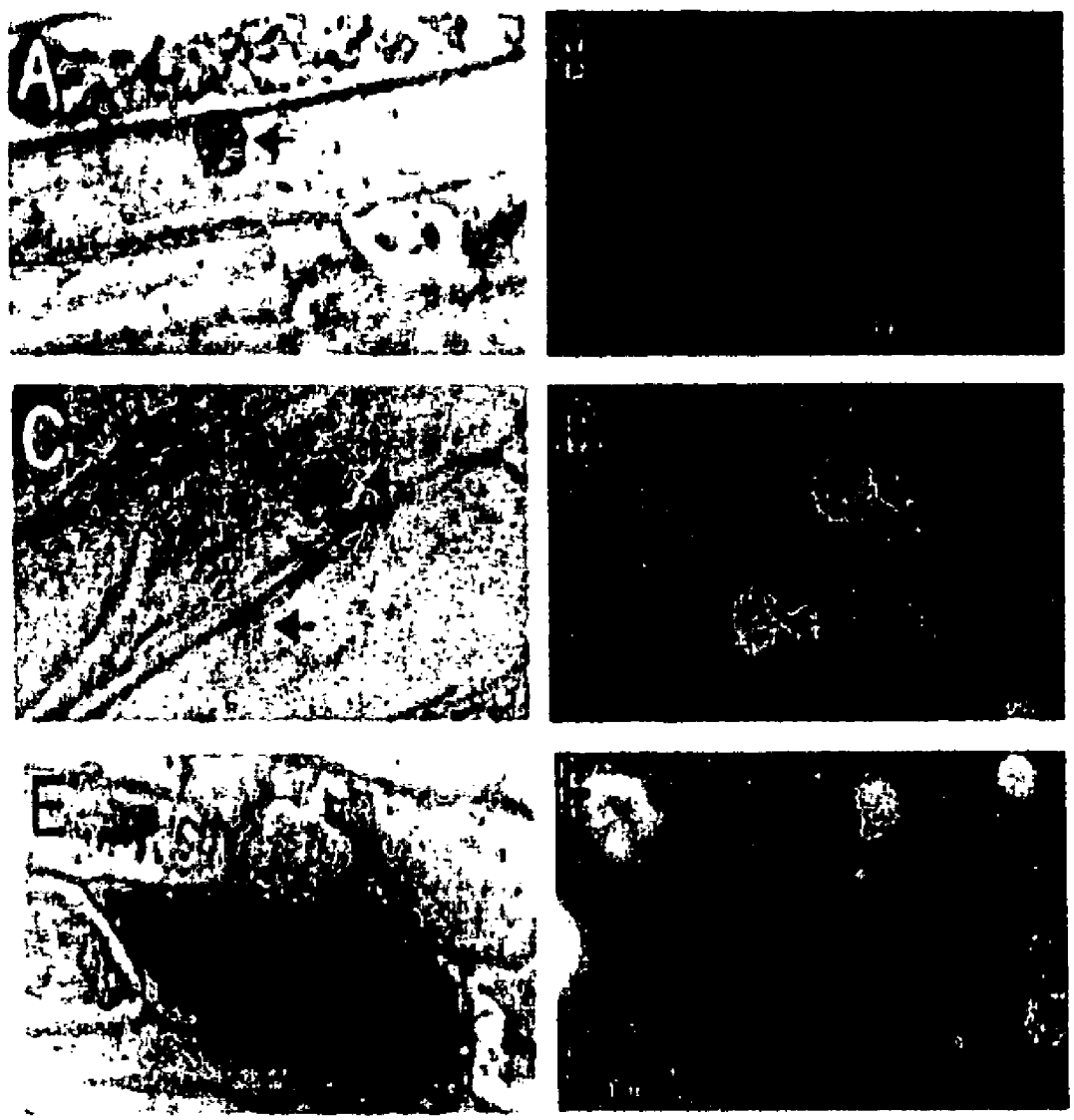
Figure: 5

STRESS RESPONSIVE TRANSCRIPTION FACTOR INVOLVED IN PLANT GROWTH AND DEVELOPMENT AND METHODS THEREOF

RELATED APPLICATIONS

This Application claims priority from co-pending Indian Application Serial No. 1146/DEL/2006, filed on May 9, 2006, which is incorporated in its entirety by reference.

FIELD OF INVENTION

The disclosure relates to the field of plant molecular biology and relates to transgenic plant over- or under-expressing a unique light-regulated transcription factor, Z-box binding factor involved in plant growth and development. It functions as regulator in light signaling pathway, early flowering and lateral root development. This disclosure also relates to method for enhancing tolerance to environmental and abiotic stresses in plants.

BACKGROUND OF THE INVENTION

Plant development and metabolic activity are regulated by several environmental factors. Light is one of the most important environmental stimuli for plant growth and development. Light is perceived by several photoreceptors: far-red and red light by phytochromes (phyA to phyE) and blue and UV-A light by cryptochromes (cry1 and cry2). Whereas cytosolic phytochromes are translocated into the nucleus upon light-mediated activation, cryptochromes are localized in the nucleus (Curr Opin Plant Biol. (2004) 7, 564-9). Significant progress has been made in understanding the functions of photoreceptors and in the identification and characterization of downstream components of light signaling pathways (Science (2000) 288, 859-863; Annu Rev Plant Biol. (2002) 53, 329-55.). Light signaling pathways likely to have strong impact by cross-talk on other signaling pathway for optimum growth and development of plant. Light is perceived by a variety of photoreceptors and transmitted by several downstream signaling components through central regulator that control developmental as well as metabolic processes including photosynthesis and assimilate allocation. It has been very recently shown that productivity of crop plants might be enhanced by overexpressing one of the central regulators of light signaling pathway (Plant Physiology (1999) 120:73-81; Proc Natl Acad Sci USA (2004) 101: 9897-9902).

*Arabidopsis thaliana* seedling development follows two distinct pathways: skotomorphogenesis or etiolation in the dark and photomorphogenesis or deetiolation in the light. The shift from skotomorphogenic to photomorphogenic development leads to a change in expression of approximately one-third of the total genes in Arabidopsis (Plant Cell (2001) 13, 2589-2607; Proc. Natl. Acad. Sci. (2001) 98, 9437-9442).

Regulation of transcription of specific genes is an important mechanism by which light regulates plant growth and development. CAB, RBCS, and CHS are well-studied genes that are upregulated by light. Investigations of the promoters of the light-inducible genes, including CAB, RBCS, and CHS, have led to identification of four commonly found light-responsive elements (LREs): G, GATA, GT1, and Z-box, which have been demonstrated to be essential for light-mediated transcriptional activity (Ann. Rev. Plant Physiol. Plant Mol. Biol. (1995) 46, 445-474; EMBO J. (1996) 15, 3732-3743; Plant J. (2002) 31, 741-753). Several LRE-specific transacting factors have been identified, and in some cases, their functions in light signaling pathways have been investigated (Semin. Cell Biol. (1994) 5, 335-346; Ann. Rev. Plant Physiol. Plant Mol. Biol. (1995) 46, 445-474; Plant Cell 9, 491-507).

SUMMARY OF THE INVENTION

The disclosure relates to transgenic plant overexpressing a unique light-regulated transcription factor, Z-box binding factor, found in plants. The disclosure further provides identification and functional characterization of Z-box binding factor in light signaling pathway, early flowering and lateral root development. The disclosure also relates to a method for modifying plant's traits, such as enhanced productivity and increased tolerance to environmental and abiotic stress.

Accordingly in one aspect, the present disclosure relates to an isolated polynucleotide sequence as shown in SEQ ID NO: 21 and SEQ ID NO: 23 encoding for a transcription factor.

Another aspect of the disclosure provides the polypeptide sequence as shown in SEQ ID NO: 22 and SEQ ID NO: 24 encoded by the polynucleotide sequence as shown in SEQ ID NO: 21 and SEQ ID NO: 23

Yet another aspect of the disclosure provides a recombinant polynucleotide sequence comprising regulatory sequences and a polynucleotide sequence as shown in SEQ ID NO: 21 coding for a transcription factor having a polypeptide sequence as shown in SEQ ID NO: 22 or a polynucleotide sequence as shown in SEQ ID NO: 23 coding for a transcription factor having a polypeptide sequence as shown in SEQ ID NO: 24.

Further aspect of the disclosure relates to a method of producing a transgenic plant having improved growth and tolerance to environmental and abiotic stresses wherein the transgenic plant comprises recombinant polynucleotide sequence of the invention.

Still further aspect of the disclosure provides a transgenic plant comprising the recombinant polynucleotide sequence of the present invention wherein said transgenic plant has improved growth and tolerance to environmental and abiotic stresses.

BRIEF DESCRIPTION OF THE FIGURES

The above objectives and advantages of the disclosed teachings will become more apparent by describing in detail preferred embodiments thereof with reference to the attached drawings in which:

FIG. 1 shows Gel Shift Assay wherein,

A. GST-AtMYC2 and the consensus dimeric Z-box LRE as probe

Lane 1: No protein (-ve control)

Lane 2: 500 ng of GST protein

Lane 3-7: Approximately 200 ng of recombinant protein was added to the radioactively labeled Z-box.

B. GST-AtMYC2 and the CAB1 minimal light-responsive promoter as probe

Lane 1: No protein (-ve control)

Lane 2: 500 ng of GST protein

Lane 3-7: Approximately 200 ng of recombinant protein was added to the radioactively labeled, 189-bp DNA fragment of the CAB1 minimal promoter.

The triangle indicates increasing concentrations of the competitors (Comp.)

Plus and minus signs indicate the presence or absence of competitors, respectively.

The asterisk indicates a spurious band present in all lanes.

Figure 2:
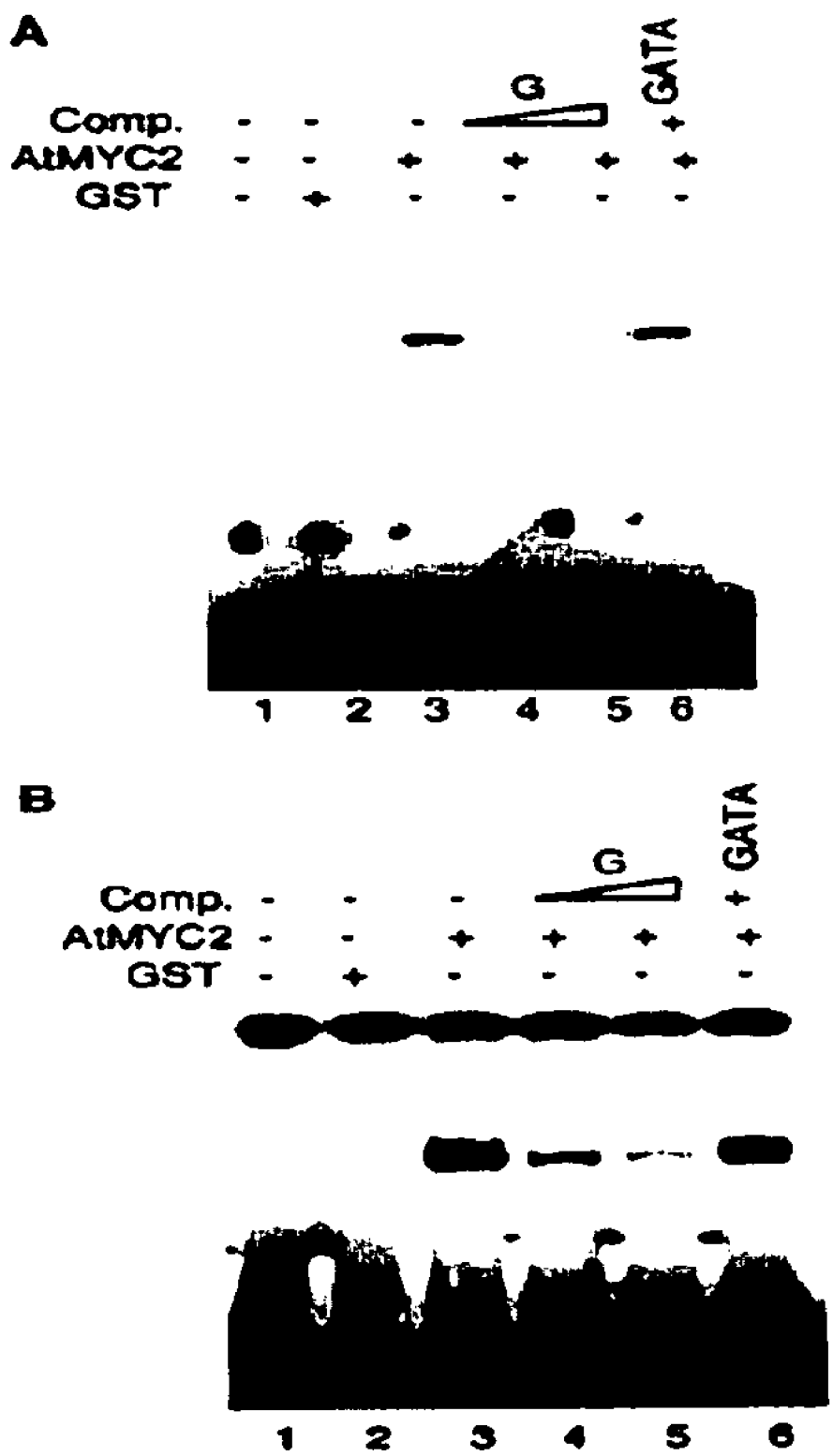

FIG. 2 shows Gel Shift Assay wherein

A. GST-AtMYC2 and the consensus tetrameric G-box LRE

Lane 1: No protein (-ve control)

Lane 2: 500 ng of GST protein

Lane 3-6: Approximately 300 ng of recombinant protein was added to the radioactively labeled G-box.

B. GST-AtMYC2 and the RBCS-1A minimal light responsive promoter

Lane 1: No protein (-ve control)

Lane 2: 500 ng of GST protein

Lane 3-6: Approximately 300 ng of recombinant protein was added to the radioactively labeled, 196-bp DNA fragment of the RBCS-1A minimal promoter.

The triangle indicates increasing concentrations of the competitors (Comp.)

Plus and minus signs indicate the presence or absence of competitors, respectively.

Figure 3:
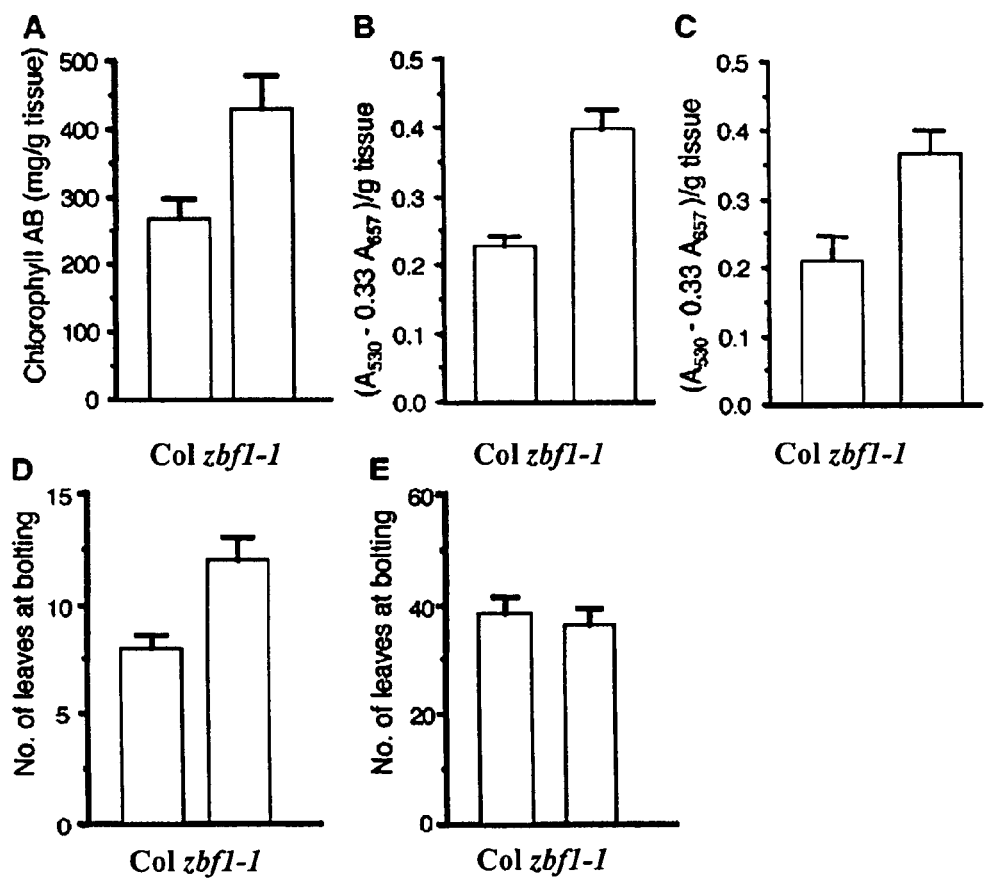

FIG. 3 shows Characterization of zbf Mutants, wherein

A. Accumulation of chlorophyll a/b in 6-d-old constant BL-grown (30 mmol/s/m$^2$) wild-type and zbf1-1 mutant seedlings.

B. Accumulation of anthocyanin in 6-d-old constant BL-grown (30 mmol/s/m$^2$) wild-type and zbf1-1 mutant seedlings.

C. Accumulation of anthocyanin in 6-d-old constant FR-grown (90 mmol/s/m$^2$) wild-type (Col) and zbf1-1 mutant seedlings.

D. Number of rosette leaves formed at the time of bolting in wild-type (Col) and zbf1-1 mutant plants grown in long-day conditions of 16 h of WL (100 mmol/s/m$^2$) and 8 h of dark.

Figure 4:
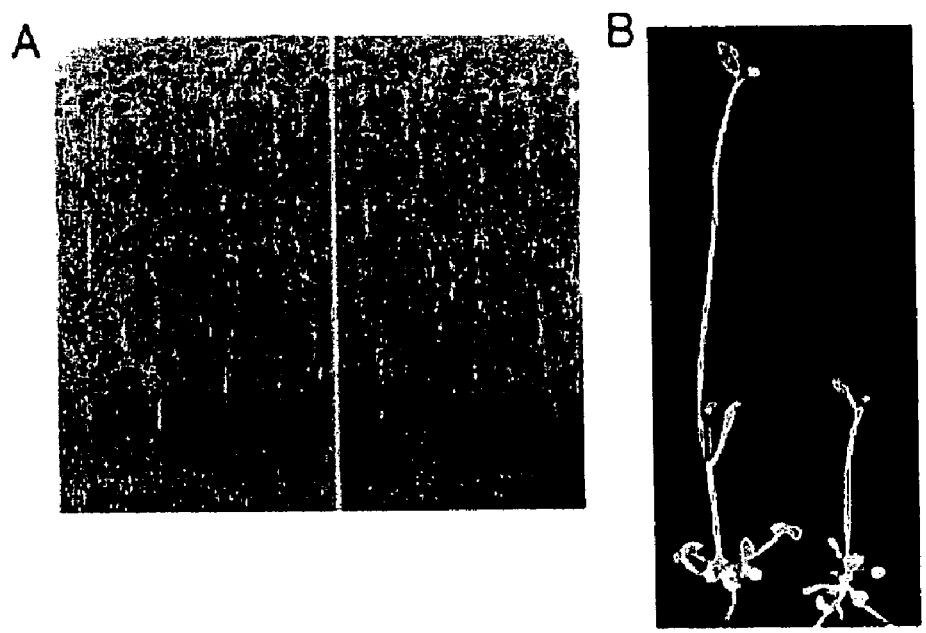

E. Number of rosette leaves formed at the time of bolting in wild-type (Col) and zbf1-1 mutant plants grown under short-day conditions of 8 h of WL (100 mmol/s/m$^2$) and 16 h of dark FIG. 4 shows the zbf1 Mutants Show Multiple Phenotypes, wherein A. The root growth of 16-d-old wild-type and zbf1-1 mutant plants grown in a long day cycle of 16 h of WL (100 mmol/s/m$^2$) and 8 h of darkness.

B. Adult plants (21 d old) grown in a long day cycle of 16 h of WL (100 mmol/s/m$^2$) and 8 h of darkness.

FIG. 5 shows constitutive nuclear localization of ZBF1, wherein

A. US-stained onion epidermal cells expressing GUS-ZBF1 after incubation in constant darkness B. DAPI-stained of A C. GUS-stained onion epidermal cells expressing GUS-ZBF1 after incubation in constant WL D. DAPI-stained of C E. GUS-stained onion epidermal cells expressing GUS after incubation in constant WL F. DAPI-stained of E

DETAILED DESCRIPTION OF THE INVENTION

The disclosure relates to transgenic plant overexpressing a unique light-regulated transcription factor, Z-box binding factor, found in plants. The disclosure further provides identification and functional characterization of Z-box binding factor in light signaling pathway, early flowering and lateral root development. The disclosure also relates to method for modifying a plant's traits, such as enhanced productivity and increased tolerance to environmental and abiotic stress.

The term "operably linked" as used herein refers to a juxtaposition wherein the components so described are in a relationship permitting them to function in their intended manner. For example a sequence is operably linked to a coding sequence if the promoter affects its transcription or expression.

The disclosure relates to the isolation and characterization of a unique light-regulated transcription factor (ZBF1) which interacts with the Z-box and G-box light responsive element of minimal light regulated promoters.

The disclosed polynucleotide sequence can be isolated from appropriate natural source or can be produced as intron free cDNA using conventional techniques.

The disclosed polynucleotide sequence may be expressed by placing them in operably linkage with suitable control sequences in a replicable expression vectors. Regulatory elements may include origin of replication, a promoter, enhancer and transcriptional terminator sequences amongst others. The selection of the regulatory sequence to be included in the expression vector is dependent on the type of host or host cell intended to be used for expressing the nucleic acid of the present invention.

One embodiment of the disclosure relates to an isolated nucleic acid molecule encoding for a transcription factor having polynucleotide sequence as shown in SEQ ID NO: 21 and SEQ ID NO: 23.

Another embodiment is a polypeptide sequence having an amino acid sequence as shown in SEQ ID NO: 22 and SEQ ID NO: 24, encoded by the nucleic acid molecule having polynucleotide sequence as shown in SEQ ID NO: 21 and SEQ ID NO: 23.

Further the disclosure provides a recombinant polynucleotide sequence comprising regulatory sequence and a polynucleotide sequence as shown in SEQ ID NO: 21 coding for a transcription factor having a polypeptide sequence as shown in SEQ ID NO: 22 or a polynucleotide sequence as shown in SEQ ID NO: 23 coding for a transcription factor having a polypeptide sequence as shown in SEQ ID NO: 24.

In another embodiment, the regulatory sequences are selected from a group consisting of CaMV, NOS, OCS, AdhI, AdhII, Ubi-1 and the native promoter of ZBF1 gene.

Yet another embodiment provides a recombinant vector comprising the recombinant polynucleotide sequence as shown in SEQ ID NO: 21 and SEQ ID NO: 23 in sense or in antisense orientation.

Still yet another embodiment of the disclosure relates to the recombinant vectors, wherein the vectors is selected from a group consisting of pCM5, pCM6, pCM21, pCM22, pSK1, pSK2, pSK3, pSK4, pSK5, pVY1, pVY2, pVY3, pVY4, pVY5, pVY6, pSNG1, pSNG2, pSNG3, pSNG4 and pSNG5.

In another embodiment the disclosure also provides a host cell comprising the recombinant vector of the invention, wherein the host cell is selected from a group consisting of E. coli, Agrobacterium and yeast.

Suitable E. coli strain is selected from a group consisting of JM101, DH5α, BL21, HB101, and XL1-Blue. The Agrobacterium strain is selected from a group consisting of LBA4404, EHA101, EHA105, GV3101 and A281.

Depending on the host cell used, transformation is performed according to the standard procedure known in the art.

In preferred embodiment the disclosure provides a method of producing a transgenic plant having improved growth and tolerance to environmental and abiotic stresses wherein the transgenic plant comprises recombinant polynucleotide sequence of the invention.

Transformation into plants can be carried out using Agrobacterium tumefaciens or other method well known in the art such as biolisitc transformation, in planta transformation and chemical method.

In further embodiment, the invention provides a method of producing the transgenic plant, said method comprising:

a. constructing a recombinant vector comprising the polynucleotide sequence as shown in SEQ ID NO: 21 or SEQ ID NO: 23 in sense or in antisense orientation.
b. mobilizing the recombinant vector into *Agrobacterium* cells to produce recombinant *Agrobacterium* cells;
c. obtaining suitable explants from said plant;
d. co-cultivating the explants with the recombinant *Agrobacterium* cells to produce transformed plant cells;
e. selecting transformed plant cells from;
f. obtaining transformed plantlets;
g. transferring transformed plantlets to soil to produce transgenic plants.

One embodiment of the disclosure is the explant used for the transformation wherein the explant is selected from a group consisting of cotyledons, hypocotyls, leaves, stem and roots.

Plants suitable for transformation with the recombinant vectors of the present disclosure may be selected from a broad range of the plants of monocotyledonous or dicotyledonous plant, wherein the monocotyledonous plant is selected from a group consisting of rice, maize, wheat, barley and sorghum and the dicotyledonous plant is selected from a group consisting of *Arabidopsis*, tobacco, tomato, pea, soybean, brassicas, carrot, chickpea, brinjal and pigeon pea.

The disclosure further provides the progeny derived from transgenic plants comprising the polynucleotide sequence as shown in SEQ ID NO: 21 or SEQ ID NO: 23 in sense or in antisense orientation.

The disclosure also provides seeds produced from the transgenic plant produced in the present invention.

Identification and Cloning of Z-Box Binding Transcription Factor (ZBF1)

In present disclosure, the applicants demonstrate that Z-box (ZBF1) transcription factor is involved in light-regulated gene expression and photomorphogenic growth in plant. Ligand binding screening was performed to screen an *Arabidopsis* cDNA expression library for Z-box binding factors (ZBFs). The functional characterization of ZBF1 factor was carried out. The details of plant growth conditions and DNA-Ligand binding screening is described in the Example 1 and Example 2.

Sequence analysis of the coding sequence of ZBF1 cDNA isolated from the ligand binding screening was carried out. ZBF1 gene from *Arabidopsis* consists of 2172 nucleotides as shown in SEQ ID NO: 21 coding for protein consisting of 623 amino acids as shown in SEQ ID NO: 22. Sequence data for SEQ ID NO: 21 and SEQ ID NO: 22 have been deposited with the EMBL/GenBank data libraries under accession number AJ843256. ZBF1 gene from tomato consists of 2123 nucleotides as shown in SEQ ID NO: 23 coding a protein of 688 amino acids as shown in SEQ ID NO: 24. Details are provided in Example 3.

Z-box (ZBF1) binding transcription factor can be cloned by various methods known in art. Various vectors can be used for cloning the transcription factors. Yeast vectors such as pBD-GAL4; pAD-GAL4 may be employed. Similarly, bacterial vectors such as pBlueScript; pUC19; pUC20; pGEX4T-2; pET20b+ may be used. The recombinant vectors comprising the nucleotide sequence coding for Z-box (ZBF1) binding transcription factor were designated as pCM5, pCM6, pSK1, pSK2, pSK3, pSK4, pSK5 pVY1, pVY2, pVY3, pVY4, pVY5, pVY6, pSNG1, pSNG2, pSNG3, pSNG4 and pSNG5.

The detailed procedure of the construction of these recombinant vectors and *E. coli* transformation is described in Example 4.

TABLE 1

Details of the recombinant vectors constructed. ZBF1 constructs made:

| Construct name | Description | Nucleotide Positions | Amino acid positions |
|---|---|---|---|
| 1. CM5, CM6 | Full length ZBF1 with GUS-GFP fusion in pCAMBIA1303 | 1 to 1776 | 1-592 |
| 2. SK1 | ZBF1 full length (over-expresser) in pCAMBIA1303 | 1 to 2100 | 1-623 |
| 3. SK2 | ZBF1 full length (antisense) in pCAMBIA1303 | 1 to 2100 in antisense | — |
| 4. SK3 | ZBF1 full length in pET20b (+) vector | 1 to 2000 | 1-623 |
| 5. SK4 | ZBF1 truncated in pET20b (+) vector | 1 to 900 | 1-300 |
|  | in pBI121 |  |  |
| 6. SK5 | ZBF1 truncated in pCAMBIA1303 | 1 to 1600 | 1-534 |
| 7. VY1 | ZBF1 full length in pGEX4T-2 vector | 1 to 1950 | 1-623 |
| 8. VY2 | ZBF1 truncated in pGAD-RP4 | 1 to 1000 | 1-334 |
| 9. VY3 | ZBF1 (−bHLH) in pGAD-RP3 | 1 to 1200 | 1-400 |
| 10. VY4 | ZBF1 truncated in pGAD-RP2 | 1 to 1500 | 1-500 |
| 11. VY5 | ZBF1 full length in pGAD-RP1 | 1 to 2000 | 1-623 |
| 12. VY6 | ZBF1 full length with native promoter in pCAMBIA1303 | 1.3 kb upstream +2 kbgene | 1-623 |
| 13. SNG1 | ZBF1 (with bHLH) in pET20b(+) vector | 1 to 495 | 381-546 |
| 14. SNG2 | ZBF1 (with bHLH) in pET20b(+) vector | 1 to 670 bp | 337-560 |
| 15. SNG3 | ZBF1 full length in pBD-GAL4 cam | 1 to 1870 | 1-623 |
| 16. SNG4 | ZBF1-N-terminal in pBD-GAL4 cam | 1 to 1293 | 1-431 |
| 17. SNG5 | ZBF1-C-terminal in pBD-GAL4 cam | 1137 to 1878 | 378-623 |

In Vitro Functional Characterization of Z-Box Binding Transcription Factor (ZBF1)

Figure 1:
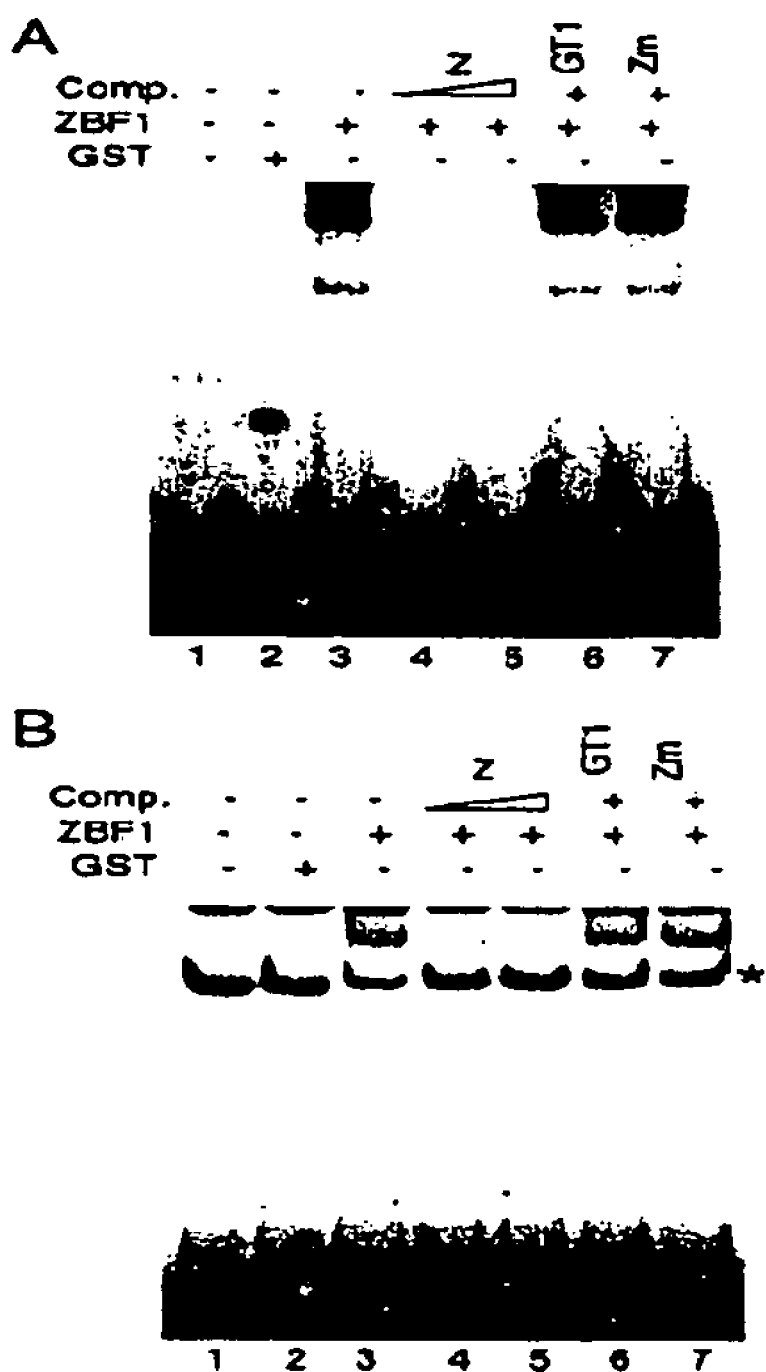

Interaction of ZBF1 transcription factor with the Z-box was studied, for this, purified glutathione S-transferase-At-MYC2 (GST-AtMYC2) fusion protein and dimeric Z-box DNA as probe in electrophoretic mobility shift (gel shift) assays. A high affinity DNA-protein complex was detected along with the free probe, as shown in FIG. 1A (lane 3). Whereas this DNA binding activity was competed out with 50 or 100 molar excess of unlabeled Z-box DNA (FIG. 1A, lanes 4 and 5), no competition was observed with 100 molar excess of GT1 or Zm, a mutated version of the Z-box (FIG. 1A, lanes 6 and 7).

The ability of ZBF1 to interact with the Z-box of native light-regulated CAB1 minimal promoter was tested. The 189-bp, light-responsive minimal promoter region of Arabidopsis CAB1 was used for gel shift assays. As shown in FIG. 1B, GST alone did not show any binding activity; however, a strong low mobility DNA-protein complex was formed with GST-AtMYC2 fusion protein (lanes 2 and 3). This DNA-protein complex was efficiently competed out with 50 and 100 molar excess of unlabeled Z-box (FIG. 1B, lanes 4 and 5) but not with 100 molar excess of GT1 or Zm (FIG. 1B, lanes 6 and 7). Taken together, these results suggest that AtMYC2 specifically interacts with Z-box LRE.

To test whether the bHLH protein ZBF1 is also able to interact with the G-box (which includes the E-box) of light-regulated promoters, gel shift assays was carried out (See Example 5) using purified GST-AtMYC2 fusion protein and a consensus tetrameric G-box LRE as probe. As shown in FIG. 2A, a low mobility DNA-protein complex was formed that was competed out by 80 and 150 molar excess of unlabeled G-box but not with 150 molar excess of unlabeled GATA LRE (FIG. 2A, lanes 3 to 6). A 196-bp minimal promoter fragment of RBCS-1A was used for gel shift assays. The minimal promoter region of RBCS-1A contains a G-box LRE, which has been demonstrated to be critical for light-mediated activation of this promoter (Donald and Cashmore, 1990). This minimal promoter fragment contains three GT1 and two GATA (or I) LREs in addition to the G-box. ZBF1 formed a strong DNA-protein complex (FIG. 2B, lane 3), which was competed out by 80 and 150 molar excess of unlabeled 26-bp double-stranded oligonucleotide containing the native G-box of RBCS-1A promoter but not with 150 molar excess of GATA (FIG. 2B, lanes 4 to 6). Taken together, these results suggest that ZBF1 interacts with both the Z-box and G-box LREs of light-regulated promoters.

Isolation and Characterization of Mutations in ZBF1

Because ZBF1 interacts with the Z-box and G-box LREs present in the light-regulated promoters of CAB1 and RBCS-1A, respectively, involvement of ZBF1 in the regulation of photomorphogenic growth in *Arabidopsis* was investigated through mutational studies. Mutants were searched in T-DNA knockout collections (Alonso et al., 2003) and a mutant line with a T-DNA insertion at the 5' end of ZBF1 coding sequence (Salk_017005) was identified, and the corresponding allele was designated as zbf1-1. The atmyc2-1 and zf1-1 alleles were already described to have less sensitivity to JA in Boter et al., 2004. Heterozygous T1 plants with the T-DNA insertion allele showed 3:1 segregation ratios with kanamycin resistance versus sensitive lines in T2 progeny, suggesting that one single T-DNA insertion locus is present in zbf1-1 mutant plants. The junctions of T-DNA and ZBF1 were amplified by PCR, and the DNA sequence analyses revealed that the T-DNA was inserted in nucleotide position 960 bp from the start codon. RNA gel blot and protein gel blot analyses were unable to detect any transcript or protein encoded by ZBF1 in zbf1-1 mutant background. Therefore, the T-DNA insertion in ZBF1 likely caused instability of the corresponding transcript, resulting in a null mutant. A second mutant line zbf1-2 with a T-DNA insertion (Salk_083483) at the 5' end of the ZBF1 coding sequence was also identified where the T-DNA was inserted in nucleotide position 1237 bp from the start codon (Boter et al., 2004).

To characterize the light regulation of ZBF1 expression, the relative levels of ZBF1 expression in 6-d-old constant dark or various light-grown wild-type seedlings were examined, including red light (RL), far-red light (FR), and blue light (BL). As shown in FIGS. 3C and 3D, ZBF1 is expressed in dark and in all light conditions tested. The levels of expression were found to be almost similar in dark and various light-grown conditions with slightly lower level in FR. These results suggest that ZBF1 is constitutively expressed in dark- and light-grown *Arabidopsis* seedlings.

ZBF1 regulates the expression of light inducible genes

RNA gel blot analyses (see Example 6) were carried out to determine the role of ZBF1 in the regulation of light-inducible gene expression, and measured the expression of CAB, RBCS, and CHS genes in 6-d-old various light-grown seedlings. The expression of the light-inducible genes was significantly elevated in zbf1-1 mutants as compared with wild-type seedlings in BL and FR. In the case of RBCS, whereas an approximately twofold increase in the transcript level was detected in BL, the expression of the gene was found to be more than threefold higher in the zbf1-1 mutant background as compared with the wild type in FR. Very little increase, if any, in the expression of CHS and CAB was detected in zbf1-1 mutants in WL; however, an approximately twofold to threefold increase was detected in BL and FR as compared with wild-type background. No significant change in expression of these genes was detected in the zbf1-1 mutant in RL. Taken together, these results suggest that ZBF1 acts as a negative regulator of CAB, RBCS, and CHS in BL- and FR-meditated expression which was not shown earlier.

To further examine the light-mediated induction of CAB, RBCS, and CHS in the zbf1-1 mutant background, 4-d-old dark-grown seedlings were transferred to BL for 2, 4, 8, and 12 h, and the transcript levels were measured. The level of induction of CAB, RBCS, and CHS genes was significantly elevated in zbf1-1 mutants as compared with wild-type seedlings at various time points. Whereas a more than eightfold induction in RBCS expression was found in zbf1-1 after 12 h, a less than fivefold induction was detected in the wild-type background. In the case of CHS, an approximately sixfold induction was detected in zbf1-1; however, an approximately fourfold induction was found in the wild-type background at 12 h. Similarly, the expression of CAB was induced to approximately fivefold in zbf1-1 mutants; however, an approximately twofold induction was detected in the wild-type background. Taken together, these results suggest that ZBF1 plays a negative regulatory role in the BL-mediated induction of CAB, RBCS, and CHS genes.

Chlorophyll and Anthocyanin Measurements

Chlorophyll and anthocyanin levels were measured following protocols as described by Holm et al. (2002). The accumulation of chlorophyll and anthocyanin are two such important physiological responses. To determine whether ZBF1 plays any role in chlorophyll or anthocyanin accumulation, we measured the chlorophyll and anthocyanin contents in wild-type and zbf1-1 mutant seedlings under various wavelengths of light. As shown in FIGS. 3A and 3B, the chlorophyll and anthocyanin contents, respectively, were significantly higher in zbf1-1 mutants as compared with wild-type seedlings in BL. Furthermore, the anthocyanin content of zbf1-1 mutant seedlings was found to be significantly higher as compared with the wild type in FR. While propagating zbf1-1 mutant plants, we observed that zbf1-1 mutation caused late flowering. Whereas long day-grown (16 h light/8 h dark) wild-type plants start flowering after the formation of approximately eight rosette leaves, the zbf1-1 mutants flower after producing; 13 rosette leaves (FIG. 3D). However, the short day-grown (8 h light/16 h dark) zbf1-1 mutant plants were unable to display such effects (FIG. 3E).

zbf1 Mutants Exhibit BL-Specific Morphological Defects in Seedling Development

The hypocotyl length of 6-d-old zbf1 mutants and wild-type seedlings grown under constant dark or white light (WL) conditions was measured. However, no significant difference in hypocotyl length was detected between wild-type and zbf1 mutant seedlings grown in constant darkness or WL conditions. To determine whether the atmyc2 mutants have any altered morphology in a particular wavelength of light, the growth of 6-d-old seedlings under various wavelengths of light, such as RL, FR, and BL was examined. The enhanced inhibition in hypocotyl elongation of zbf1 was observed in constant BL; however, no significant change in hypocotyl length was observed in constant FR or RL. Measurements of hypocotyl length revealed that 6-d-old BL-grown zbf1 mutant seedlings had significantly shorter hypocotyls as compared with wild-type seedlings with no significant change in RL or FR at various fluences. These results suggest that ZBF1 acts as a negative regulator of BL-mediated photomorphogenic growth.

Although FR-grown zbf1 mutants did not show any altered morphology, the mutant seedlings had higher accumulation of anthocyanin at the junction of hypocotyls and cotyledons a characteristic of hyperphotomorphogenic growth during early seedling development in *Arabidopsis*. Examination of root growth of zbf1 mutant plants revealed that 16-d-old mutant plants developed significantly less lateral roots as compared with wild-type plants (FIG. 4A). Furthermore, whereas zbf1 mutant seedlings did not exhibit any altered morphology while grown in various fluences of WL, the mutant adult plants exhibited significantly short stature as compared with WL-grown wild-type plants (FIG. 4B). Taken together, these results suggest that ZBF1 acts as a negative regulator of photomorphogenesis and its effect is more pronounced under BL condition. These results further demonstrate that ZBF1 acts as a positive regulator of lateral root formation.

A genomic fragment containing ZBF1 and its upstream sequence of 1.5 kb was introduced into the zbf1-1 mutant plants for a complementation test. The transgenic seedlings were unable to display a BL-specific hypersensitive response, suggesting that the observed phenotypes of zbf1 mutants were caused by the loss of ZBF1 function. Loss of function of ZBF1 leads to enhanced sensitivity to BL irradiation. However, the transgenic seedlings overexpressing ZBF1 did not show significant change in sensitivity to WL or BL, although the transcript levels of ZBF1 in these lines were dramatically elevated. Interestingly, overexpression of a truncated version of ZBF1 with 110 amino acid deleted from the N-terminal end resulted in elongated hypocotyls in BL as compared to wild type.

Epistasis analysis was carried out to determine the involvement of photoreceptors in ZBF1 function. The zbf1 cry1 and zbf1 cry2 double mutants displayed similar hypocotyl lengths as zbf1 mutant seedlings in BL. However, zbf1 phyA double mutants exhibited a hypocotyl length similar to phyA mutant seedlings in BL. These results suggest that zbf1 is epistatic to cry1 and cry2; however, phyA is likely to be epistatic to zbf1 in BL.

ZBF1 is Constitutively Localized in the Nucleus

It has been demonstrated that the light dependent shuttling of COP1, a negative regulator of photomorphogenesis, between cytosol and nucleus is crucial for photomorphogenic growth in *Arabidopsis*. Since ZBF1 has a nuclear localization signal and it also acts as a negative regulator of photomorphogenesis, the subcellular localization of ZBF1-GUS fusion protein was examined in a transient assay system in onion epidermal cells. The uidA gene, which encodes β-glucouronidase (GUS), was fused in frame to the coding sequence of ZBF1, and the expression of the fusion gene was driven by CaMV 35S promoter. As shown in FIG. 5, ZBF1-GUS protein was present in the nucleus under constant dark and WL conditions (FIG. 5A-D), whereas GUS protein alone was detected throughout the cytoplasm (FIG. 5E-F). These results demonstrate that nuclear localization of ZBF1 is independent of light stimuli (See Example 7).

zbf1 Mutants are Less Sensitive to ABA and JA Responsiveness

It was previously shown that mutation in ZBF1 (generated by an Ac/Ds tagging system) caused *Arabidopsis* plants to be less sensitive to ABA (Abe et al., 2003). Furthermore, it has been recently demonstrated that jin1-1 mutants are less sensitive to JA (Lorenzo et al., 2004). To determine whether zbf1 mutants respond to ABA and JA in a similar fashion, the effect of ABA and JA on zbf1-1 mutant plants was monitored. Seeds of wild-type and mutant plants were plated on MS plates without or with various concentrations of ABA. Whereas 1 mM ABA reduced the rate of germination of wild-type seeds, the effect was significantly suppressed in zbf1-1 mutants. However, no noticeable effect of ABA on growth of the zbf1-1 mutants, which were germinated in 1 mM ABA, was observed as compared with wild-type plants.

Plant Transformation

Binary vectors such as pBI101.2, pCAMBIA and pBI121 may be used for construction of plant expression vectors. Construction of the binary vectors may be carried out by various methods well known in art. It can be done by ligation of the cDNA in sense or antisense orientation into the binary vector wherein the cDNA is linked to regulatory sequences. The recombinant plant transformation vectors comprising the nucleotide sequence (SEQ ID NO: 21 or SEQ ID NO: 23) either in sense or in antisense orientation were designated as pCM5, pCM6, pSK1, pSK2 and pSK5 (see Table 1 for details).

For the generation of over expresser line of ZBF1, full-length cDNA was amplified by PCR and the fragment was cloned in pCAMBIA 1303 vector. For the complementation test, a genomic fragment containing full-length ZBF1 and; 1.5-kb upstream DNA sequence was amplified by PCR and the fragment was cloned into pBI101.2 vector. The *Agrobacterium tumefaciens* strain GV3101 was transformed individually with each recombinant construct. The *Arabidopsis* wild-type (Wassilewskija) plants (for over expression) or zbf1-1 mutant plants (for complementation) were transformed with the recombinant plasmid or empty vector by the floral dip method, and transgenic plants were selected on 15-mg/ml hygromycin plates.

Several transgenic lines homozygous for each transgene were generated for further studies. For ABA- or JA-responsive experiments, MS plates containing 0.5, 1, or 2 mM ABA or 20 mM JA were used for monitoring growth of atmyc2-3 mutant and wild-type plants.

Plant transformation was carried out by various methods well known in the art such as *Agrobacterium*-mediated transformation, biolisitc transformation; in planta transformation and electroporation. Detailed description of the preparation of the plant transformation vectors and method for plant transformation is described in Example 8.

Several mutant lines were identified and homozygous mutant lines for ZBF1 gene were generated for further studies. The detailed procedure is described in Example 9.

Several regulatory components of photomorphogenesis from a ligand-binding screen have been identified using Z-box DNA as probe, and found that these genes are intimately involved in plant growth and development. One such regulator Z-box binding factor 1 (ZBF1) is a bHLH transcription factor. Analyses of ZBF1 knockout lines have revealed that the mutant plants have higher sensitivity to light and are dwarf and hyper-photomorphogenic in nature. Consistently, the over-expresser transgenic lines of ZBF1 displayed opposite effects. The enhanced responsiveness to light leads to higher photosynthetic performance, and altered allocations of assimilates. It has been found that ZBF1 controls the photosynthetic ability of the plants by regulating the expression of light inducible genes. Therefore, ZBF1 is an important regulatory component in photomorphogenesis that is useful in enhancing agricultural crop productivity. The short stature of the ZBF1 knockout lines clearly supports this notion. Most high yielding varieties of crop plants that are routinely used for cultivation have short stature. Several regulatory components of photomorphogenesis besides the flowering genes have been demonstrated to control flowering time in higher plants.

The flowering time in *Arabidopsis* plants gets severely delayed in ZBF1 knockout lines. And consistently over-expression of ZBF1 causes early flowering. This has been tested in crop plants such as carrot and tomato. The initial results indicate that overexpression of ZBF1 transcription factor in transgenic carrot plants (T1) leads to early flowering. Therefore, ZBF1 is an important candidate gene that is useful in reducing the generation time in higher plants. This has not been demonstrated earlier.

Other function of the ZBF1 transcription factor also analyzed and it was found that ZBF1 also promotes the formation of lateral roots. The zbf1 mutants have significantly less number of lateral roots than wild type plants. This function of ZBF1 is useful in crop plants by generating overexpressing transgenic lines that might be stress tolerant such as drought. It's important to note here that ZBF1 also acts as a transcriptional regulator in absicic acid responsive pathways, which plays an important role in stress physiology in higher plants.

While the invention is broadly as defined above, it will be appreciated by those persons skilled in the art that it is not limited thereto and that it also includes embodiments of which the following description gives examples.

EXAMPLES

It should be understood that the following examples described herein are for illustrative purposes only and that various modifications or changes in light will be suggested to persons skilled in the art and are to be included within the spirit and purview of this application and the scope of the appended claims.

Example 1

Plant Materials and Growth Conditions

Surface-sterilized seeds of Arabidopsis thaliana were sown on MS plates, kept at 4° C. in darkness for 3 to 5 days and transferred to specific light conditions at 22° C. The intensities of continuous light sources used are as follows: WL (100, 30, 15, and 5 mmol/s/m2), BL (30, 20, 15, and 5 mmol/s/m2), RL (95, 30, 15, and 5 mmol/s/m2), and FR (90, 30, 15, and 5 mmol/s/m2). Unless otherwise mentioned, the highest light intensities were used for the experiments.

Example 2

DNA-Ligand Binding Screening

A DNA-ligand binding screening was set up to identify and clone ZBF(s). Ligand binding screening was performed following the protocol of Singh et al. (1988) with some modifications. A cDNA expression library of 5-d old constant light-grown *Arabidopsis* seedlings was constructed in λZapII vector. Freshly prepared 150-mm NZY-agar plates (5 g NaCl, 2 g MgSO4, 5 g yeast extract, 10 g NZ amine [casein hydrolysate], and 15 g agar in one liter of water) were used for plating; 10,000 pfu/plate and incubated for 4 to 6 h at 37° C. These plates were overlaid with nitrocellulose membrane (soaked in 10 mM isopro-pylthio-b-galactoside solution for 20 min, then dried briefly by keeping on Whatman filter paper) when the tiny plaques started to develop and incubated for 6 to 8 h at 37° C. These plates were then transferred from 37° C. to 4° C. for 15 min and marked. The membrane was then lifted off the plate and immersed in 50 ml of blocking solution per membrane. After incubation at room temperature for 1 h, the membrane was washed three times with 50 ml of TNE (15 mM Hepes, pH 7.5, 50 mM KCl, 1 mM EDTA, 1 mM DTT, 1 mM MgCl2, and 5% glycerol) for 5 min. The membrane was incubated at room temperature with 3' end-labeled Z-box and 250 mg of sonicated and denatured calf thymus DNA. The membrane was washed three times with 50 ml of TNE for 10 min, dried and autoradiographed. Putative positive plaques were picked up by aligning the autorad with the membrane and the plate. The putative clones were subjected to further screening (secondary and tertiary) following the same procedure.

2×106 clones of a cDNA expression library were screened, made of 5-d-old constant white light-grown seedlings, using a dimeric Z-box LRE as probe. (SEQ ID NOs: 1, 2, 3, 4 and 5). One sequence, ZBF1 having SEQ ID NO: 21, represented by four independent cDNA clones, were selected here for further analysis. To determine the binding specificity of the clone (ZBF1) obtained from tertiary screening, the plaques were blotted onto the membrane and cut the membrane into two halves: one half was probed with the Z-box and the other half was probed with either the GT1 or GATA LRE. Whereas a strong binding activity was found with the Z-box, no such binding activity was detected with the GATA or GT1 LRE (SEQ ID NOs: 1, 2, 3, 4, and 5) suggesting that ZBF1 specifically interacts with the Z-box.

| | |
|---|---|
| 5'-ATCTATTCGTATACGTGTCAC-3' | SEQ ID NO: 1 |
| 5'-AAGATAAGATT-3' | SEQ ID NO: 2 |
| 5'-TGTGTGGTTAATATG-3' | SEQ ID NO: 3 |
| 5'-TGACACGTGGCA-3' | SEQ ID NO: 4 |
| 5'-CTATTCGTATtCaTaTCACGTCATG-3' | SEQ ID NO: 5 |

Example 3

Sequence Analysis

The coding sequence of ZBF1 cDNA isolated from the ligand binding screening appeared to be a full-length cDNA (Atlg32640). It codes for a protein of 623 amino acids (predicted molecular mass of 68 kD) with a bHLH domain.

Deletion analyses of *Arabidopsis* CAB1 promoter have demonstrated that the Z-box is essential for the light-dependent developmental expression of CAB1 (Ha and An, 1988). Furthermore, combinatorial interactions of Z-box with other LREs have revealed that the Z-box containing synthetic as well as native promoters are regulated by several components of the light signaling pathways (Puente et al., 1996; Yadav et al., 2002). In general, the bHLH proteins are demonstrated to be interacting with the hexameric DNA sequence referred to as E-box (CANNTG). Depending on the phylogenetic analysis, bHLH proteins have been divided into four monophyletic groups (Ledent and Vervoort, 2001). One such group binds to the ACGTG core sequence, which is included in the Z-box (ATACGTGT).

Example 4

Cloning of Z-Box Transcription Factor

For the construction of various recombinant vectors, PCR was carried out using the Taq polymerase and a set of convergent primers. A 50 μl reaction mixture contained 10-20 ng DNA template, 100 μM of each primers, 1 μl of 10 mM dNTPs, 5 μl of 10× Taq buffer and 2.5 units of Taq DNA polymerase. Thirty cycles of PCR were carried out, each cycle consisting of four steps, initial denaturation at 95° C. for 2 min, denaturation at 94° C. for 1 min, annealing at 56° C. for 1 min, and extension at 72° C. for 3 min. Then the aliquot of the reaction was run on 1% agarose gels to check the amplification of the product.

ZBF1 gene was cloned in *E. coli* expression vector. For cloning the coding region of ZBF1 in protein expression vector pGEX4T-2, the ZBF1 coding region amplified by PCR by using the gene specific forward primer, FP2-bHLH (SEQ ID NO: 6) and a reverse primer, RP2-bHLH (SEQ ID NO: 7) with SmaI and NotI restriction sites.

```
                                           SEQ ID NO: 6
5'-TGGCCTCCGGCGTCGACGACAACC-3'

SEQ ID NO: 7
5'-ATAAGAATGCGGCCGCATATCAATATATACAAGTTTACTC-3'
```

The PCR amplified fragment was 2.0 kb in size and it was gel purified. The 2.0 kb fragment and pGEX4T-2 vector were digested with SmaI and NotI restriction enzymes and ligated to get the construct pGEX4T-2-ZBF1, which was transformed into DH5α cells for ZBF1 overexpression.

In the case of yeast or Agrobacterium strains, first the recombinant vector was constructed and subcloned in *E. coli* cells. The recombinant vector was then isolated from *E. coli* and used for transforming yeast or *Agrobacterium* cells for further studies.

Similarly other recombinant vectors were constructed as described above were designated as pCM5, pCM6, pSK1, pSK2, pSK3, pSK4, pSK5, pVY1, pVY2, pVY3, pVY4, pVY5, pVY6, pSNG1, pSNG2, pSNG3, pSNG4 and pSNG5 (see Table 1 for details).

*E. coli* Transformation

One ml overnight grown culture was used to freshly re-inoculate 100 ml LB (10 g tryptone, 5 g yeast extract, and 5 g NaCl/l) so that the initial O.D. becomes 0.2, and it was allowed to grow at 37° C. shaker till the O.D reached at 0.5-0.8 (2-3 h). The cells were chilled in ice for 1 hr. The cells were then harvested by centrifugation at 5000 rpm for 10 min. The pellet was re-suspended in 20 ml of ice-cold 50 mM CaCl2 solution and centrifuged at 5000 rpm for 10 min and the pellet was re-suspended in 2 ml of ice-cold 50 mM CaCl2 solution. The cells were then suspended in 50 mM CaCl2 solution and kept in ice overnight and then on the next day 15% glycerol was added. The cell (0.1 ml) suspension was then aliquot into eppendorf tubes, quickly frozen in liquid N2 and stored at −80° C.

DH5α strain was used for the transformation of ligated DNA fragments. The different DNA fragments used in this study were ligated to the appropriate vector by T4 DNA ligase by overnight incubation at 16 or 22° C. The ligation mixture was added to the competent cells and mixed gently by tapping and cells were kept in ice for 40 min. All the steps of transformation were carried out in laminar hood under sterile conditions. After 40 min of ice incubation, the cells were subjected to heat shock at 42° C. for 90 sec and quick chilled in ice for 5 minutes followed by addition of 0.9 ml of LB and allowed to grow at 37° C. with gentle shaking. An aliquot of these competent cells was plated on LB plate containing appropriate antibiotic. Blue white selection was carried out by plating 10 μg IPTG and 1 μg X-gal before plating the transformed cells. The plates were incubated at 37° C. overnight.

Example 5

Electrophoretic Mobility Shift (Gel Shift) Assays

GST-AtMYC2 was induced using 1 mM isopropylthio-b-galactoside and over expressed in *Escherichia coli*. The overexpressed GST-AtMYC2 was affinity purified using standard procedures. The DNA binding assays were performed at room temperature in a final volume of 30 ml with a binding buffer of 15 mM Hepes, pH 7.5, 35 mM KCl, 1 mM EDTA, 6% glycerol, 1 mM DTT, 1 mM MgCl2, and 2 mg of poly (dI-dC). The samples were incubated at room temperature for 15 min and then run on to 6 to 8% polyacrylamide gel at 12 to 15 mA. After drying, the gels were autoradiographed.

The 42-bp DNA fragment containing the Z-box dimer or 46-bp DNA fragments containing the tetrameric G-box cloned in pBluescript SK+ were digested with XhoI and HindIII, purified, and 3' end labeled with [a-32P]dCTP. The labeling of the DNA probes was carried out using standard methods well known in the art. The mutant Zm-box cloned in pBluescript was digested with EcoRI-BamHI and purified for competition studies. The tetrameric GT1 or GATA elements were purified after digestion with HindIII-XhoI and used for competition reactions. The 189-bp DNA fragment of CAB1 minimal promoter region was cloned into pBlueScript vector after PCR with forward (SEQ ID NO: 8) and reverse primer (SEQ ID NO: 9) using genomic DNA as template. The 189-bp and 196-bp fragments of native CAB1 and RBCS-1A promoters, respectively, were digested with EcoRI-BamHI, purified, and 3' end labeled for use as probe for the DNA binding assay. These assays were carried using standard methods well known in the art. One nanogram of labeled DNA was used for each binding reaction

```
5'-CGGAATTCA-TAAGGATAGAGAGATCTATTC-3'    SEQ ID NO: 8

5'-                                       SEQ ID NO: 9
CGGGATCCTGAG-GTTGCTATTGGCTAGTCAT-3'
```

Example 6

RNA Gel Blot and Protein Gel Blot Analysis

Total RNA was extracted using standard methods, and RNA gel blot analysis with 20 mg of total RNA for each sample was performed essentially as described in (Nucl. Acids Res. (2003) 31, 5256-5265). The 1.8-kb ZBF1 DNA fragment was used as probe after random prime labeling. The DNA fragments of CAB, RBCS, and CHS genes were used for probes as described by Cell (1991) 71, 791-801. The 18S rRNA was used as loading control. For protein gel blot analysis, affinity-purified ZBF1 polyclonal antibodies were used. Protein extracts were prepared from 6-d-old constant WL-grown wild-type and zbf1 mutant seedlings. Twenty micrograms of total protein was used for protein gel blot analysis. A cross-reacting band was used as a loading control.

Example 7

Nuclear Localization Studies

The 1.9 kb full length cDNA containing was amplified by PCR using forward primers FP8 (SEQ ID NO: 10) and reverse primer RP5 (SEQ ID NO: 11) and cloned into BglII-SpeI site of pCAMBIA 1303-GUS.

```
FP8:
5'-
GAAGATCTGATGACTGATTACCGGCTACAACC-3'   SEQ ID NO: 10

RP5:
5'-GACTAGTAACCACCGACATACTC-3')         SEQ ID NO: 11
```

The transcription of GUS-ZBF1 fusion is driven by the CaMV 35S promoter. Onion epidermal cells were transfected with either pCAMBIA-GUS or GUS-ZBF1 plasmids using helium biolistic gun, and incubated in constant white light or in darkness for 48 hours at 22° C. The location of β-glucouronidase activity was determined by using X-gluc and the nuclei were identified using the DNA specific stain DAPI (1 μg/ml). The subcellular localization of GUS activity was visualized using microscope and compared with the DAPI staining in the same cells using the fluorescence optics and photographs were taken.

Example 8

Plant Transformation

Construction of Plant Transformation Vectors

For the generation of over expresser lines of ZBF1, full-length cDNA was amplified by PCR using the forward primer (SEQ ID NO: 12) and reverse primer (SEQ ID NO: 13) and cloned into the BglII-SpeI site of the pCAMBIA1303 vector. For the complementation test, a genomic fragment containing full-length ZBF1 and; 1.5-kb upstream DNA sequence was amplified by PCR using the forward primer (SEQ ID NO: 14) and reverse primer (SEQ ID NO: 15) and cloned into the SmaI site of the pBI101.2 vector.

```
5'-GACTAGTAATCG-TAGCTTTTGCAGCTTC-3'      SEQ ID NO: 12

5'-GACTAGTATACAGACTCA-AACATAGAGC-3'      SEQ ID NO: 13

5'-                                      SEQ ID NO: 14
TCCCCCGGGGAGTAATGGGACCA-TATTGGTG-3'

5'-                                      SEQ ID NO: 15
TCCCCCGGGTATCAATATATACAAGT-TTACTC-3'
```

*Agrobacterium* Transformation

The recombinant vectors were transformed into *Agrobacterium tumefaciens* GV3101 and LBA4404 according to standard methods well known in the art. The *Agrobacterium tumefaciens* strain GV3101 was transformed individually with each recombinant constructs namely pCM5, pCM6, pSK1, pSK2 and pSK5.

Recombinant plasmid construct was transformed into *Agrobacterium* by freeze thaw method. For the preparation of competent cells, *Agrobacterium tumefaciens* strain was grown in 50 ml YEM medium (0.04% yeast extract, 1% mannitol, 0.01 NaCl, 0.02% MgSO4.7H2O and 0.05% K2HPO4) at 28° C. with vigorous shaking until the O.D600 reached 0.5 to 0.6. The culture was chilled in ice and centrifuged at 3000 g for 5 min at 4° C. The pellet was re-suspended in 1 ml ice cold CaCl2 (20 mM) and 0.1 ml aliquots were dispensed in pre-chilled eppendorf tubes and stored at −80° C.

Transformation of *Agrobacterium* with various vector constructs was carried out by mixing 1 μg of DNA with competent cells followed by immediate freezing in liquid nitrogen. Subsequently cells were thawed, incubated the eppendorf tubes at 37° C. for 5 minutes and then 1 ml of YEM medium was added to the tube and incubated at 28° C. for 6 hrs. Cells were spread on a YEM agar plate supplemented with appropriate concentration of vector specific antibiotics and incubated at 28° C. Transformed colonies that appeared after 1-2 days were analyzed either by PCR or by colony hybridization and the positive colonies were confirmed by restriction digestion of the purified recombinant plasmid.

*Arabidopsis* Transformation

The *Arabidopsis* wild-type (Wassilewskija) plants (for overexpression) or zbf1 mutant plants (for complementation) were transformed with the recombinant plasmid or empty vector by the floral dip method, and transgenic plants were selected on 15-mg/ml hygromycin plates. Several transgenic lines homozygous for each transgene were generated for further studies. For ABA- or JA-responsive experiments, MS plates containing 0.5, 1, or 2 mM ABA or 20 mM JA were used for monitoring growth of zbf1-1 mutant and wild-type plants.

Molecular Analysis of *Arabidopsis* Transformants

One or two leaves of the plants were frozen in liquid nitrogen and ground in 200 μl chromosomal DNA extraction buffer (200 mM TrisHCl pH 7.5, 250 mM NaCl, 25 mM EDTA pH 8.0, 0.5% SDS). The suspension was then centrifuged at 13000 rpm for 5 min and the supernatant was transferred to fresh tube. Supernatant was extracted with Phenol: Chloroform:Isoamyl alchohol (25:24:1) and the upper aqueous layer was transferred to fresh tube. The DNA was precipitated with 150 μl of isopropanol and pelleted by centrifuging at 13000 rpm for 5 min. The pellet was washed with 70% ethanol, dried and dissolved in 50 μl of sterile water.

Three independent T-DNA tagged lines (Alonso et al., 2003) for ZBF1 were screened separately by genomic PCR using the two gene specific primers and the LBP primer for T-DNA. The genomic DNA from the plants to be screened was isolated and PCR was carried out using that genomic DNA and gene specific primers LP2, RP2, LP5, RP5, LP7, RP7 and T-DNA primer LBP. When three primers (two gene specific and one T-DNA primer) were used, PCR product of 900 bp was obtained from wild type plant and above 400 bp size of fragment was obtained from the homozygous, both the bands one wild type plant and other homozygous plant were obtained from the heterozygous plant. When only LP and RP gene specific primers were used, PCR product of 900 bp was obtained from wild type plant; no amplification from homozygous plant; PCR product consisting of DNA fragments of two sizes were obtained from heterozygous plant. The plants which were detected as homozygous by PCR analysis were selected and seeds were bulked from these homozygous plants and further checked by RT-PCR.

Carrot Transformation

Recombinant *Agrobacterium* strains containing pCAMBIA-ZBF1 construct were used to inoculate 20 ml of YEB media (Beef Extract 0.5%; Yeast Extract 0.1%; Peptone 0.5%; Sucrose 0.5%; MgSO4, 7H2O 0.49 g; Agar 1.5%;

pH-6.8-7.0) containing rifampicin (5 μg/ml) and kanamycin (25 μg/ml). Cells were incubated at 28° C./160 rpm for overnight. Next day, 1 ml of overnight culture was used to inoculate 50 ml of YEB containing rifampicin (5 μg/ml) and kanamycin (25 μg/ml) and culture was incubated at 28° C./160 rpm till O.D600 reached at 0.6. 25 ml×2 of this culture was transferred to a centrifuge tube and spanned at 3000 rpm for 5 min at room temperature. Supernatant was discarded and the pellet was completely resuspended in 50 ml of liquid MS media containing 2,4-D (1 ppm) and BAP (0.1 ppm). The dilution of *Agrobacterium* used for transformation was 1:2. The 1:2 diluted culture was transferred to 90×10 Petri plates.

Seeds of carrot (*Daucus carota* cv—Pusa kesar) were washed with 5% Teepol detergent for 5 min and washed thoroughly in running water. These seeds were sterilized with 0.1% of HgCl2 for 5-7 min and washed thoroughly with sterile water for three to four times in Laminar Hood. Sterilized seeds were inoculated in MS (½×) for 20 days. After 20 days, carrot explants (½ inches long hypocotyls: pricked randomly with sterile needle) were kept in MS plates containing 2,4-D (1 ppm) and BAP (0.1 ppm) in dark condition for overnight. Overnight incubated carrot explants (½ inches long) were dipped in 1:2 diluted *Agrobacterium* culture for 10 min. These explants were dried on sterile autoclaved Whatmann (3 mm) filter paper spread on 150×15 mm Petri plates. These explants were again transferred back to the same MS plates with 2,4-D (1 ppm) and BAP (0.1 ppm) and kept in dark for two days. After two days, explants were transferred to MS/cephotoxime (250 mg/L) and incubated for 20 days until the callus formation. Calli were transferred to MS/Hyg-B plates (5-10 μg/ml) along with 2,4-D (1 ppm) and BAP (0.1 ppm). After 15 days, subculture in same media was performed. Calli were transferred to MS media and transformants were selected for further analysis.

Molecular Analysis of Carrot Transformants

The transformed lines were tested by Western blots to determine the level of ZBF1 protein. After hardening and transferring into soil, several independent transformed plants with higher level of ZBF1 protein were selected for the generation of homozygous transgenic plants for further studies.

Example 9

Generation of Double Mutants

For the generation of double mutants, such as zbf1 cry1, zbf1 cry2, and zbf1 phyA, homozygous zbf1-1 mutant plants were crossed individually with hy4-2.23N, cry2-1, and phyA-101 homozygous mutant lines. In the F2 generation, seedlings were grown in WL (60 mmol/s/m2) or FR (30 mmol/s/m2) for the identification of cry1, cry2, or phyA homozygous lines, and elongated seedlings were selected and transferred to soil. To determine the genotype at the ZBF1 locus, 40 seedlings from each line were tested by genomic PCR. F3 progeny that are homozygous for zbf1-1 mutant plants were further examined and considered as zbf1 cry1, zbf1 cry2, and zbf1 phyA double mutants. Because zbf1 (atmyc2), cry1, cry2, and phyA were of different ecotype backgrounds, F2 seedlings, which were mutant for cry1, cry2, or phyA but homozygous for the wild-type ZBF1, were used as control.

Obtaining Homozygous Mutant Lines

To obtain the homozygous zbf1-1 or zbf1-2 mutant line, plants heterozygous or homozygous for the zbf1-1 (atmyc2-3) or zbf1-2 mutation were subjected to PCR genotyping analyses. Individual plants were examined by PCR using the left border specific primer (SEQ ID NO: 16) and the ZBF1 specific primers (SEQ ID NO: 17) and RP2 (SEQ ID NO: 18) for atmyc2-3 and LP5 (SEQ ID NO: 19) and RP5 (SEQ ID NO: 20) for zbf1-2.

| | | |
|---|---|---|
| LBP: | 5'-GCG-TGGACCGCTTGCTGCACCT-3' | SEQ ID NO: 16 |
| LP2: | 5'-GATCTGATTCTCCGGCGGTTT-3' | SEQ ID NO: 17 |
| RP2: | 5'-GTTCGCCGCTTTC-TACTC-3' | SEQ ID NO: 18 |
| LP5: | 5'-CGGCGAGCTCGAGTTTCACTT-3' | SEQ ID NO: 19 |
| RP5: | 5'-AATTATCCGGGTCGGGTTGTG-3' | SEQ ID NO: 20 |

What is claimed is:

1. An isolated nucleic acid molecule encoding for a transcription factor having the polynucleotide sequence as shown in SEQ ID NO: 23.

2. A recombinant polynucleotide sequence comprising a regulatory sequence and the polynucleotide sequence as shown in SEQ ID NO: 23 and coding for a transcription factor having the polypeptide sequence as shown in SEQ ID NO: 24.

3. The recombinant polynucleotide sequence of claim 2, wherein the regulatory sequence is selected from the group consisting of CaMV, NOS, OCS, AdhI, AdhII, Ubi-1 and the native promoter of ZBF1 gene.

4. A recombinant vector comprising the recombinant polynucleotide sequence of claim 2.

5. The recombinant vector of claim 4, wherein said polynucleotide sequence is in a sense orientation.

6. The recombinant vector of claim 4, wherein the recombinant vector is pSK1.

7. An isolated host cell comprising the recombinant vector of claim 4.

8. The host cell of claim 7, wherein said host cell is selected from the group consisting of *E. coli, Agrobacterium* and yeast.

9. The *E. coli* host cell of claim 8, wherein the *E. coli* is selected from a the group consisting of JM101, DH5α, BL21, HB101, and XL1-Blue.

10. The *Agrobacterium* host cell of claim 8, wherein the *Agrobacterium* is selected from a the group consisting of LBA4404, EHA101, EHA105, GV311 and A281.

11. A transgenic plant comprising the isolated polynucleotide sequence as shown in SEQ ID NO:23 and coding for a transcription factor having the polypeptide sequence as shown in SEQ ID NO: 24.

12. The transgenic plant of claim 11, wherein the transgenic plant comprises the polynucleotide sequence as shown in SEQ ID NO: 23 in a sense orientation.

13. The transgenic plant of claim 11, wherein the transgenic plant is selected from the group consisting of a monocotyledonous and a dicotyledonous plant.

14. The transgenic plant of claim 13, wherein the monocotyledonous plant is selected from the group consisting of rice, maize, wheat, barley and sorghum.

15. The transgenic plant of claim 13, wherein the dicotyledonous plant is selected from the group consisting of *Arabidopsis*, tobacco, tomato, pea, soybean, brassicas, carrot, chickpea, brinjal and pigeon pea.

16. The transgenic plant of claim 13, wherein the dicotyledonous plant is selected from the group consisting of *Arabidopsis*, tomato and carrot.

17. A progeny derived from the transgenic plant of claim 11, wherein the progeny comprises the isolated polynucleotide sequence as shown in SEQ ID NO:23 and coding for a transcription factor having the polypeptide sequence as shown in SEQ ID NO:24.

18. A seed produced from the transgenic plant of claim 11, wherein the seed comprises the isolated polynucleotide sequence as shown in SEQ ID NO:23 and coding for a transcription factor having the polypeptide sequence as shown in SEQ ID NO:24.

19. A method of producing a transgenic plant, said method comprises introducing the isolated polynucleotide sequence as shown in SEQ ID NO:23 coding for a transcription factor having the polypeptide sequence as shown in SEQ ID NO:24.

20. The method of producing the transgenic plant of claim 19, wherein said method is selected from the group consisting of *Agrobacterium*-mediated transformation, biolistic transformation, in planta transformation and chemical method.

21. The method of producing the transgenic plant of claim 20, wherein the *Agrobacterium*-mediated transformation method comprises:
   a. constructing a recombinant vector comprising the polynucleotide sequence as shown in SEQ ID NO:23;
   b. mobilizing the recombinant vector of step (a) into *Agrobacterium* cell to produce a recombinant *Agrobacterium* cell;
   c. obtaining an explant from a plant;
   d. co-cultivating the explant of step (c) with the recombinant *Agrobacterium* cell of step (b) to produce a transformed plant cell;
   e. selecting the transformed plant cell from step (d) to obtain a transformed plantlet; and
   f. transferring the transformed plantlet to soil to produce the transgenic plant.

22. The method of producing the transgenic plant of claim 21, wherein the recombinant vector is pSK1.

23. The method of producing the transgenic plant of claim 21, wherein the recombinant vector comprises the polynucleotide sequence as shown in SEQ ID NO: 23 in a sense orientation.

24. The method of producing the transgenic plant of claim 21, wherein the *Agrobacterium* cell is selected from the group consisting of LBA4404, EHA101, EHA105, GV3101 and A 281.

25. The method of producing the transgenic plant claim 21, wherein the explant is selected from a the group consisting of cotyledons, hypocotyls, leaves, stem and roots.

26. The method of producing the transgenic plant of claim 21, wherein the plant is selected from a the group consisting of a monocotyledonous plant and a dicotyledonous plant.

27. The method of producing the transgenic plant of claim 26, wherein the monocotyledonous plant is selected from the group consisting of rice, maize, wheat, barley and sorghum.

28. The method of producing the transgenic plant of claim 26, wherein the dicotyledonous plant is selected from the group consisting of *Arabidopsis*, tobacco, tomato, pea, soybean, brassicas, carrot, chickpea, brinjal and pigeon pea.

29. The method of producing the transgenic plant claim 26, wherein the dicotyledonous plant is selected from the group consisting of *Arabidopsis*, tomato and carrot.

30. The transgenic plant of claim 11, wherein said transgenic plant has improved growth and tolerance to environmental and abiotic stresses.

31. The method of producing a transgenic plant of claim 19, wherein said method produces a transgenic plant with improved growth and tolerance to environmental and abiotic stresses.

* * * * *

SEQUENCE LISTING

<160> NUMBER OF SEQ ID NOS: 24

<210> SEQ ID NO 1
<211> LENGTH: 21
<212> TYPE: DNA
<213> ORGANISM: Artificial
<220> FEATURE:
<223> OTHER INFORMATION: Synthetic sequence

<400> SEQUENCE: 1
atctattcgt atacgtgtca c                                        21

<210> SEQ ID NO 2
<211> LENGTH: 11
<212> TYPE: DNA
<213> ORGANISM: Artificial
<220> FEATURE:
<223> OTHER INFORMATION: Synthetic sequence

<400> SEQUENCE: 2
aagataagat t                                                   11

<210> SEQ ID NO 3
<211> LENGTH: 15
<212> TYPE: DNA
<213> ORGANISM: Artificial
<220> FEATURE:
<223> OTHER INFORMATION: Synthetic sequence

<400> SEQUENCE: 3
tgtgtggtta atatg                                                    15

<210> SEQ ID NO 4
<211> LENGTH: 12
<212> TYPE: DNA
<213> ORGANISM: Artificial
<220> FEATURE:
<223> OTHER INFORMATION: Synthetic sequence

<400> SEQUENCE: 4
tgacacgtgg ca                                                       12

<210> SEQ ID NO 5
<211> LENGTH: 25
<212> TYPE: DNA
<213> ORGANISM: Artificial
<220> FEATURE:
<223> OTHER INFORMATION: Synthetic sequence

<400> SEQUENCE: 5
ctattcgtat tcatatcacg tcatg                                         25

<210> SEQ ID NO 6
<211> LENGTH: 24
<212> TYPE: DNA
<213> ORGANISM: Artificial
<220> FEATURE:
<223> OTHER INFORMATION: Synthetic sequence

<400> SEQUENCE: 6
tggcctccgg cgtcgacgac aacc                                          24

<210> SEQ ID NO 7
<211> LENGTH: 40
<212> TYPE: DNA
<213> ORGANISM: Artificial
<220> FEATURE:
<223> OTHER INFORMATION: Synthetic sequence

<400> SEQUENCE: 7
ataagaatgc ggccgcatat caatatatac aagtttactc                         40

<210> SEQ ID NO 8
<211> LENGTH: 30
<212> TYPE: DNA
<213> ORGANISM: Artificial
<220> FEATURE:
<223> OTHER INFORMATION: Synthetic sequence

<400> SEQUENCE: 8
cggaattcat aaggatagag agatctattc                                    30

<210> SEQ ID NO 9
<211> LENGTH: 31
<212> TYPE: DNA
<213> ORGANISM: Artificial
<220> FEATURE:

<223> OTHER INFORMATION: Synthetic sequence

<400> SEQUENCE: 9
cgggatcctg aggttgctat tggctagtca t                            31

<210> SEQ ID NO 10
<211> LENGTH: 32
<212> TYPE: DNA
<213> ORGANISM: Artificial
<220> FEATURE:
<223> OTHER INFORMATION: Synthetic sequence

<400> SEQUENCE: 10
gaagatctga tgactgatta ccggctacaa cc                           32

<210> SEQ ID NO 11
<211> LENGTH: 23
<212> TYPE: DNA
<213> ORGANISM: Artificial
<220> FEATURE:
<223> OTHER INFORMATION: Synthetic sequence

<400> SEQUENCE: 11
gactagtaac caccgacata ctc                                     23

<210> SEQ ID NO 12
<211> LENGTH: 28
<212> TYPE: DNA
<213> ORGANISM: Artificial
<220> FEATURE:
<223> OTHER INFORMATION: Synthetic sequence

<400> SEQUENCE: 12
gactagtaat cgtagctttt gcagcttc                                28

<210> SEQ ID NO 13
<211> LENGTH: 28
<212> TYPE: DNA
<213> ORGANISM: Artificial
<220> FEATURE:
<223> OTHER INFORMATION: Synthetic sequence

<400> SEQUENCE: 13
gactagtata cagactcaaa catagagc                                28

<210> SEQ ID NO 14
<211> LENGTH: 31
<212> TYPE: DNA
<213> ORGANISM: Artificial
<220> FEATURE:
<223> OTHER INFORMATION: Synthetic sequence

<400> SEQUENCE: 14
tcccccgggg agtaatggga ccatattggt g                            31

<210> SEQ ID NO 15
<211> LENGTH: 32
<212> TYPE: DNA
<213> ORGANISM: Artificial
<220> FEATURE:
<223> OTHER INFORMATION: Synthetic sequence

<400> SEQUENCE: 15
tcccccgggt atcaatatat acaagtttac tc                           32

```
<210> SEQ ID NO 16
<211> LENGTH: 22
<212> TYPE: DNA
<213> ORGANISM: Artificial
<220> FEATURE:
<223> OTHER INFORMATION: Synthetic sequence

<400> SEQUENCE: 16
gcgtggaccg cttgctgcac ct                                              22

<210> SEQ ID NO 17
<211> LENGTH: 21
<212> TYPE: DNA
<213> ORGANISM: Artificial
<220> FEATURE:
<223> OTHER INFORMATION: Synthetic sequence

<400> SEQUENCE: 17
gatctgattc tccggcggtt t                                               21

<210> SEQ ID NO 18
<211> LENGTH: 18
<212> TYPE: DNA
<213> ORGANISM: Artificial
<220> FEATURE:
<223> OTHER INFORMATION: Synthetic sequence

<400> SEQUENCE: 18
gttcgccgct ttctactc                                                   18

<210> SEQ ID NO 19
<211> LENGTH: 21
<212> TYPE: DNA
<213> ORGANISM: Artificial
<220> FEATURE:
<223> OTHER INFORMATION: Synthetic sequence

<400> SEQUENCE: 19
cggcgagctc gagtttcact t                                               21

<210> SEQ ID NO 20
<211> LENGTH: 21
<212> TYPE: DNA
<213> ORGANISM: Artificial
<220> FEATURE:
<223> OTHER INFORMATION: Synthetic sequence

<400> SEQUENCE: 20
aattatccgg gtcgggttgt g                                               21

<210> SEQ ID NO 21
<211> LENGTH: 2172
<212> TYPE: DNA
<213> ORGANISM: Arabidopsis thaliana

<400> SEQUENCE: 21
actacgaaga ctttctccta tctctctctc tctcattaaa aacgtgtttt tttttaccgg     60
tcaccggttt atggaatgac tgattaccgg ctacaaccaa cgatgaatct ttggaccacc    120
gacgacaacg cttctatgat ggaagctttc atgagctctt ccgatatctc aactttatgg    180
cctccggcgt cgacgacaac cacgacggcg acgactgaaa caactccgac gccggcgatg    240
gagattccgg cacaggcggg atttaatcaa gagactcttc agcaacgttt acaagctttg    300
attgaaggaa cacacgaagg ttggacctac gctatattct ggcaaccgtc gtatgatttc    360
```

-continued

```
tccggcgcct ccgtgctcgg atggggagat ggttattaca aaggtgaaga agataaagca      420
aacccgagac ggagatcgag ttcgccgccg ttttctactc cggcggatca ggagtacagg      480
aaaaaagtgt tgagagagct taactcgttg atctccggtg gtgttgctcc gtcggatgac      540
gctgttgatg aggaggtgac ggatacggaa tggttttttct tggtttcgat gacgcagagc      600
ttcgcttgcg gtgcgggatt agctggtaaa gcgtttgcaa cgggtaacgc ggtttgggtt      660
tccgggtcag atcaattatc cgggtcgggt tgtgaacggg ctaagcaagg aggagtgttt      720
gggatgcata ctattgcgtg tattccttcg gcgaacggag ttgtggaagt cgggtcaacg      780
gagccgatcc gacagagttc ggaccttatt aacaaggttc gaattctttt caatttcgac      840
ggcggagctg gagatttatc gggtcttaat tggaatcttg acccggatca aggtgagaac      900
gacccgtcta tgtggattaa tgacccgatt ggaacacctg gatctaacga accgggtaac      960
ggagctccaa gttctagctc ccagctttt tcaaagtcta ttcagtttga aacggtagc      1020 tcaagcacaa taaccgaaaa cccgaatctg gatccgactc cgagtccggt tcattctcag      1080
acccagaatc cgaaattcaa taacactttc tcccgagaac ttaattttc gacgtcaagt      1140 tctactttag tgaaaccaag atccggcgag atattaaact tcggcgatga aggtaaacga      1200
agctccggaa acccggatcc aagttcttat tcgggtcaaa cacaattcga aaacaaaaga      1260
aagaggtcga tggttttgaa cgaagataaa gttctatcat tcggagataa aaccgccgga      1320
gaatcagatc actccgatct agaagcttcc gtcgtgaaag aagtagcagt agagaaacgt      1380
ccaaagaaac gaggaagaaa gccagcaaac ggtagagaag agccactaaa ccacgtcgaa      1440
gcagagagac aaagacgcga gaaactaaac caaagattct acgcgttacg agcggttgta      1500
ccaaacgttt caaaaatgga taaagcttcg ttactcggtg acgcaatcgc ttacatcaac      1560
gagcttaaat ccaaagtagt caaaacagag tcagagaaac tccaaatcaa gaaccagctc      1620
gaggaagtga aactcgagct cgccggaaga aaagcgagtg ctagtggagg agatatgtcg      1680
tcttcgtgtt cttcgattaa accggtgggg atggagattg aagtgaagat aattggttgg      1740
gacgcaatga ttagagttga atctagtaag aggaatcatc cggcggcgag ttgatgtcg      1800 gcgttgatgg atttggagtt ggaagtgaat cacgcgagta tgtcggtggt taacgatttg      1860
atgattcaac aagcgacggt gaagatgggt tttaggatct atacgcaaga acagctcaga      1920
gcaagtttga tttcaaaaat cggttaaaag ggtgtgtttt gggaagttta gaaagttatg      1980
gggtcaaatc ataattaatt cgttttagtg gcttcagtaa ttttgtagat tttagtttg      2040 taagaaaaaa atcttaaaat agagcgacaa gtttcttctt ttgctctatg tttgagtctg      2100
tatcgtttta ttgttgtatc tcctcaatga gtaaacttgt atatattgat atgagtaata      2160
tgagttagtt ac                                                         2172
```

<210> SEQ ID NO 22
<211> LENGTH: 622
<212> TYPE: PRT
<213> ORGANISM: Arabidopsis thaliana

<400> SEQUENCE: 22

```
Met Thr Asp Tyr Arg Leu Gln Pro Thr Met Asn Leu Trp Thr Thr Asp
1               5                   10                  15

Asp Asn Ala Ser Met Met Glu Ala Phe Met Ser Ser Ser Asp Ile Ser
            20                  25                  30

Thr Leu Trp Pro Pro Ala Ser Thr Thr Thr Thr Ala Thr Thr Glu
        35                  40                  45
```

-continued

```
Thr Thr Pro Thr Pro Ala Met Glu Ile Pro Ala Gln Ala Gly Phe Asn
     50                  55                  60

Gln Glu Thr Leu Gln Gln Arg Leu Gln Ala Leu Ile Glu Gly Thr His
 65                  70                  75                  80

Glu Gly Trp Thr Tyr Ala Ile Phe Trp Gln Pro Ser Tyr Asp Phe Ser
                 85                  90                  95

Gly Ala Ser Val Leu Gly Trp Gly Asp Gly Tyr Tyr Lys Gly Glu Glu
             100                 105                 110

Asp Lys Ala Asn Pro Arg Arg Ser Ser Pro Pro Phe Ser Thr
         115                 120                 125

Pro Ala Asp Gln Glu Tyr Arg Lys Lys Val Leu Arg Glu Leu Asn Ser
     130                 135                 140

Leu Ile Ser Gly Gly Val Ala Pro Ser Asp Asp Ala Val Asp Glu Glu
145                 150                 155                 160

Val Thr Asp Thr Glu Trp Phe Phe Leu Val Ser Met Thr Gln Ser Phe
                 165                 170                 175

Ala Cys Gly Ala Gly Leu Ala Gly Lys Ala Phe Ala Thr Gly Asn Ala
             180                 185                 190

Val Trp Val Ser Gly Ser Asp Gln Leu Ser Gly Ser Gly Cys Glu Arg
             195                 200                 205

Ala Lys Gln Gly Gly Val Phe Gly Met His Thr Ile Ala Cys Ile Pro
     210                 215                 220

Ser Ala Asn Gly Val Val Glu Val Gly Ser Thr Glu Pro Ile Arg Gln
225                 230                 235                 240

Ser Ser Asp Leu Ile Asn Lys Val Arg Ile Leu Phe Asn Phe Asp Gly
                 245                 250                 255

Gly Ala Gly Asp Leu Ser Gly Leu Asn Trp Asn Leu Asp Pro Asp Gln
             260                 265                 270

Gly Glu Asn Asp Pro Ser Met Trp Ile Asn Asp Pro Ile Gly Thr Pro
     275                 280                 285

Gly Ser Asn Glu Pro Gly Asn Gly Ala Pro Ser Ser Ser Gln Leu
     290                 295                 300

Phe Ser Lys Ser Ile Gln Phe Glu Asn Gly Ser Ser Thr Ile Thr
305                 310                 315                 320

Glu Asn Pro Asn Leu Asp Pro Thr Pro Ser Pro Val His Ser Gln Thr
                 325                 330                 335

Gln Asn Pro Lys Phe Asn Asn Thr Phe Ser Arg Glu Leu Asn Phe Ser
             340                 345                 350

Thr Ser Ser Ser Thr Leu Val Lys Pro Arg Ser Gly Glu Ile Leu Asn
         355                 360                 365

Phe Gly Asp Glu Gly Lys Arg Ser Ser Gly Asn Pro Pro Ser Ser Tyr
     370                 375                 380

Ser Gly Gln Thr Gln Phe Glu Asn Lys Arg Lys Arg Ser Met Val Leu
385                 390                 395                 400

Asn Glu Asp Lys Val Leu Ser Phe Gly Asp Lys Thr Ala Gly Glu Ser
                 405                 410                 415

Asp His Ser Asp Leu Glu Ala Ser Val Val Lys Glu Val Ala Val Glu
             420                 425                 430

Lys Arg Pro Lys Lys Arg Gly Arg Lys Pro Ala Asn Gly Arg Glu Glu
         435                 440                 445

Pro Leu Asn His Val Glu Ala Glu Arg Gln Arg Arg Glu Lys Leu Asn
     450                 455                 460

Gln Arg Phe Tyr Ala Leu Arg Ala Val Val Pro Asn Val Ser Lys Met
```

```
                465                 470                 475                 480

Asp Lys Ala Ser Leu Leu Gly Asp Ala Ile Ala Tyr Ile Asn Glu Leu
                485                 490                 495

Lys Ser Lys Val Val Lys Thr Glu Ser Glu Lys Leu Gln Ile Lys Asn
            500                 505                 510

Gln Leu Glu Glu Val Lys Leu Glu Leu Ala Gly Arg Arg Ala Ser Ala
            515                 520                 525

Ser Gly Gly Asp Met Ser Ser Ser Cys Ser Ser Ile Lys Pro Val Gly
    530                 535                 540

Met Glu Ile Glu Val Lys Ile Ile Gly Trp Asp Ala Met Ile Arg Val
545                 550                 555                 560

Glu Ser Ser Lys Arg Asn His Pro Ala Ala Arg Leu Met Ser Ala Leu
                565                 570                 575

Met Asp Leu Glu Leu Glu Val Asn His Ala Ser Met Ser Val Val Asn
            580                 585                 590

Asp Leu Met Ile Gln Gln Ala Thr Val Lys Met Gly Phe Arg Ile Tyr
            595                 600                 605

Thr Gln Glu Gln Leu Arg Ala Ser Leu Ile Ser Lys Ile Gly
        610                 615                 620

<210> SEQ ID NO 23
<211> LENGTH: 2123
<212> TYPE: DNA
<213> ORGANISM: Lycopersicum esculatum (Tomato)

<400> SEQUENCE: 23
actagtgatt gtgtttatgg aatgactgaa tacagcttgc ccaccatgaa tttgtggaac     60
aatagtacta gcgatgataa cgtttctatg atggaagctt tatgtcttc tgatctttct    120 ttttgggcta ctaataattc tacttctgct gctgcggttg tgtcaattc aaatcttcct    180 catgctagta gtaatactcc ctctgttttt gcaccatctt cttctacatc tgcatctact    240
ttatccgcag ctgcgactgt ggatgcttcc aaatctatgc cgttttttcaa ccaagaaacc    300 cttcagcagc gtcttcaagc tcttattgat ggtgctagag agacgtggac ttatgctatc    360
ttttggcaat cgtcggttgt tgatttctca agtccgtctg tgttgggttg gggagatggt    420
tattacaaag gggaagaaga taaagcaaaa aggaaattat cggtgtcatc acctgcttat    480
attgctgagc aggagcatcg gaagaaggtt ctacgggagc tgaattcgtt gatttccggg    540
gcaccacccg gaacggatga tgcggttgat gaagaagtta ccgacaccga atggttcttt    600
cttatctcca tgacccaatc gtttgttaat ggaagtgggc ttcctggtca ggcgttgtat    660
agttccagcc cgatttgggt cgccggaact gagaaattgg cagcttcaca ctgtgaacgt    720
gtgaggcaag cacaagggtt cgggctccag acgattgtct gtattccttc agctaacggc    780
gtggttgaat tgggctcgac ggagttgatt gttcaaagtt ctgatcttat gaacaaggtt    840
agagtattgt ttaacttcag taatgatttg ggttctggtt catgggctgt gcagccggag    900
agcgacccat cggcgctctg gctcactgat ccatcgtcct caggtatgga agttagagag    960
tctttaaata cagttcaaac aaattcagtt ccatctagta atagtaataa gcaaattgct   1020
tatgaaaatg agaataatca tccatctgga aatggtcaga gttgttacaa tcagcaacaa   1080
cagaagaatc ctcctcagca acaaacacaa ggactcttca cgagggagtt gaattttcg   1140 gaattcggtt tcgatggaag tagtaatagg aatggaaatt catcggtttc ttgcaagcct   1200
gaatcaggag aaatcttgaa ttttggtgat agtactaaaa aaagtgcttc cagtgccaat   1260
```

-continued

```
gtgaacttgt ttacaggtca gtcccaattt ggggctgggg aggagaataa taacaagaac      1320
aagaaaagat cagctacttc caggggaagc aatgaagaag gaatgctttc atttgtttca      1380
ggtacagtgg tgccttcttc gggcatgaag tcaggtggag gcggaggcga agactctgaa      1440
cattcagatc tcgaggcttc agtggtgaaa gaagctgata gtagtagagt ggtagagcct      1500
gaaaagaggc caaggaagcg aggtagaaag ccagcgaatg gacggagga gccattgaat      1560 cacgtcgagg cagagaggca aaggaggag aaattgaacc aaagattcta cgcgcttaga      1620
gctgttgtac caaatgtgtc taagatggac aaggcatcac tccttggaga tgctatttcc      1680
tatataaacg agttgaaatc gaagcttcaa aatacagagt cagataaaga agacttgaag      1740
agccaaatag aagatttaaa gaaagaatca aggcgccccg gtcctcctcc accaccaaat      1800
caagatctca agatgtctag ccacactgga ggcaagattg tagacgtgga tatagacgtt      1860
aagatcatcg gatgggatgc aatgattcgt atacaatgta ataaaaagaa tcatccagcc      1920
gcaaggctaa tggcagcgct catggaatta gacctagacg tgcatcatgc cagtgtttca      1980
gttgtcaacg atttgatgat ccaacaagcc acagtgaaaa tgggtagcag gaattacact      2040
gaagagcagc ttagggtagc gttgacatcg aaaattgctg aaacacacta aaccccttag      2100
aaagtagata gaaatcgtca atc                                              2123
```

<210> SEQ ID NO 24
<211> LENGTH: 688
<212> TYPE: PRT
<213> ORGANISM: Lycopersicum esculatum (Tomato)

<400> SEQUENCE: 24

```
Met Thr Glu Tyr Ser Leu Pro Thr Met Asn Leu Trp Asn Asn Ser Thr
1               5                   10                  15

Ser Asp Asp Asn Val Ser Met Met Glu Ala Phe Met Ser Ser Asp Leu
            20                  25                  30

Ser Phe Trp Ala Thr Asn Asn Ser Thr Ser Ala Ala Ala Val Gly Val
        35                  40                  45

Asn Ser Asn Leu Pro His Ala Ser Ser Asn Thr Pro Ser Val Phe Ala
    50                  55                  60

Pro Ser Ser Thr Ser Ala Ser Thr Leu Ser Ala Ala Ala Thr Val
65                  70                  75                  80

Asp Ala Ser Lys Ser Met Pro Phe Phe Asn Gln Glu Thr Leu Gln Gln
                85                  90                  95

Arg Leu Gln Ala Leu Ile Asp Gly Ala Arg Glu Thr Trp Thr Tyr Ala
            100                 105                 110

Ile Phe Trp Gln Ser Ser Val Val Asp Phe Ser Ser Pro Ser Val Leu
        115                 120                 125

Gly Trp Gly Asp Gly Tyr Tyr Lys Gly Glu Glu Asp Lys Ala Lys Arg
    130                 135                 140

Lys Leu Ser Val Ser Ser Pro Ala Tyr Ile Ala Glu Gln Glu His Arg
145                 150                 155                 160

Lys Lys Val Leu Arg Glu Leu Asn Ser Leu Ile Ser Gly Ala Pro Pro
                165                 170                 175

Gly Thr Asp Asp Ala Val Asp Glu Glu Val Thr Asp Thr Glu Trp Phe
            180                 185                 190

Phe Leu Ile Ser Met Thr Gln Ser Phe Val Asn Gly Ser Gly Leu Pro
        195                 200                 205

Gly Gln Ala Leu Tyr Ser Ser Ser Pro Ile Trp Val Ala Gly Thr Glu
    210                 215                 220
```

-continued

```
Lys Leu Ala Ala Ser His Cys Glu Arg Val Arg Gln Ala Gln Gly Phe
225                 230                 235                 240

Gly Leu Gln Thr Ile Val Cys Ile Pro Ser Ala Asn Gly Val Val Glu
            245                 250                 255

Leu Gly Ser Thr Glu Leu Ile Val Gln Ser Ser Asp Leu Met Asn Lys
            260                 265                 270

Val Arg Val Leu Phe Asn Phe Ser Asn Asp Leu Gly Ser Gly Ser Trp
        275                 280                 285

Ala Val Gln Pro Glu Ser Asp Pro Ser Ala Leu Trp Leu Thr Asp Pro
    290                 295                 300

Ser Ser Ser Gly Met Glu Val Arg Glu Ser Leu Asn Thr Val Gln Thr
305                 310                 315                 320

Asn Ser Val Pro Ser Ser Asn Ser Asn Lys Gln Ile Ala Tyr Gly Asn
                325                 330                 335

Glu Asn Asn His Pro Ser Gly Asn Gly Gln Ser Cys Tyr Asn Gln Gln
            340                 345                 350

Gln Gln Lys Asn Pro Pro Gln Gln Gln Thr Gln Gly Leu Phe Thr Arg
        355                 360                 365

Glu Leu Asn Phe Ser Glu Phe Gly Phe Asp Gly Ser Ser Asn Arg Asn
    370                 375                 380

Gly Asn Ser Ser Val Ser Cys Lys Pro Glu Ser Gly Glu Ile Leu Asn
385                 390                 395                 400

Phe Gly Asp Ser Thr Lys Lys Ser Ala Ser Ala Asn Val Asn Leu
                405                 410                 415

Phe Thr Gly Gln Ser Gln Phe Gly Ala Gly Glu Glu Asn Asn Asn Lys
            420                 425                 430

Asn Lys Lys Arg Ser Ala Thr Ser Arg Gly Ser Asn Glu Glu Gly Met
        435                 440                 445

Leu Ser Phe Val Ser Gly Thr Val Val Pro Ser Ser Gly Met Lys Ser
    450                 455                 460

Gly Gly Gly Gly Gly Glu Asp Ser Glu His Ser Asp Leu Glu Ala Ser
465                 470                 475                 480

Val Val Lys Glu Ala Asp Ser Ser Arg Val Val Glu Pro Glu Lys Arg
                485                 490                 495

Pro Arg Lys Arg Gly Arg Lys Pro Ala Asn Gly Arg Glu Glu Pro Leu
            500                 505                 510

Asn His Val Glu Ala Glu Arg Gln Arg Arg Glu Lys Leu Asn Gln Arg
        515                 520                 525

Phe Tyr Ala Leu Arg Ala Val Val Pro Asn Val Ser Lys Met Asp Lys
    530                 535                 540

Ala Ser Leu Leu Gly Asp Ala Ile Ser Tyr Ile Asn Glu Leu Lys Ser
545                 550                 555                 560

Lys Leu Gln Asn Thr Glu Ser Asp Lys Glu Asp Leu Lys Ser Gln Ile
                565                 570                 575

Glu Asp Leu Lys Lys Glu Ser Arg Arg Pro Gly Pro Pro Pro Pro
            580                 585                 590

Asn Gln Asp Leu Lys Met Ser Ser His Thr Gly Gly Lys Ile Val Asp
        595                 600                 605

Val Asp Ile Asp Val Lys Ile Ile Gly Trp Asp Ala Met Ile Arg Ile
    610                 615                 620

Gln Cys Asn Lys Lys Asn His Pro Ala Ala Arg Leu Met Ala Ala Leu
625                 630                 635                 640
```

```
                                  -continued
Met Glu Leu Asp Leu Asp Val His His Ala Ser Val Ser Val Val Asn
            645                 650                 655

Asp Leu Met Ile Gln Gln Ala Thr Val Lys Met Gly Ser Arg Asn Tyr
            660                 665                 670

Thr Glu Glu Gln Leu Arg Val Ala Leu Thr Ser Lys Ile Ala Glu Thr
            675                 680                 685
```